(12) United States Patent
Kunisada et al.

(10) Patent No.: US 9,006,201 B2
(45) Date of Patent: Apr. 14, 2015

(54) PROPHYLACTIC OR THERAPEUTIC AGENT FOR DIABETES

(75) Inventors: Rie Kunisada, Kanagawa (JP); Hirokazu Matsumoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/808,364

(22) PCT Filed: Jul. 7, 2011

(86) PCT No.: PCT/JP2011/065628
§ 371 (c)(1),
(2), (4) Date: Jan. 4, 2013

(87) PCT Pub. No.: WO2012/005339
PCT Pub. Date: Jan. 12, 2012

(65) Prior Publication Data
US 2013/0109744 A1    May 2, 2013

(30) Foreign Application Priority Data

Jul. 8, 2010  (JP) ................................ 2010-156261

(51) Int. Cl.
| | | |
|---|---|---|
| C12N 15/11 | (2006.01) | |
| C12Q 1/68 | (2006.01) | |
| C07H 21/02 | (2006.01) | |
| A61K 31/7088 | (2006.01) | |
| A61K 31/7105 | (2006.01) | |
| C12N 15/113 | (2010.01) | |

(52) U.S. Cl.
CPC ............ *C07H 21/02* (2013.01); *A61K 31/7088* (2013.01); *A61K 31/7105* (2013.01); *C12N 15/113* (2013.01); *C12N 2310/141* (2013.01)

(58) Field of Classification Search
None
See application file for complete search history.

(56) References Cited

U.S. PATENT DOCUMENTS

2009/0202624 A1    8/2009  Inazawa et al.

FOREIGN PATENT DOCUMENTS

| JP | 2008-247818 | 10/2008 |
|---|---|---|
| JP | 2009-100687 | 5/2009 |
| JP | 2009-171861 | 8/2009 |
| JP | 2009-171876 | 8/2009 |
| KR | 10-2009-0081125 | 7/2009 |
| WO | 2005/013901 | 2/2005 |
| WO | WO 2005013901 A2 * | 2/2005 |
| WO | 2006/128245 | 12/2006 |
| WO | 2007/081720 | 7/2007 |
| WO | 2007/081740 | 7/2007 |
| WO | WO 2008061537 A2 * | 5/2008 |
| WO | 2009/099465 | 8/2009 |
| WO | 2009/108866 | 9/2009 |
| WO | 2009/126726 | 10/2009 |
| WO | 2010/005295 | 1/2010 |
| WO | 2010/013864 | 2/2010 |
| WO | 2010/016638 | 2/2010 |

OTHER PUBLICATIONS

Rane et al (Cellular Imaging, 2010, 22, 7, 1054.*
A note concerning Esau et al, WO 2005/013901, document: only relevant pages of reference presented, because of the length of publication (854 pages).*
Jensen et al, Coronary heart disease in young Type 1 (insulin-dependent) diabetic patients with and without diabetic nephropathy: incidence and risk factors, 1987, Diabetologia, 30: 144-148.*
International Search Report issued Oct. 4, 2011 in International (PCT) Application No. PCT/JP2011/065628.
M. Poy et al., "A pancreatic islet-specific microRNA regulates insulin secretion", Letters to Nature, vol. 432, Nov. 2004, pp. 226-230.
N. Yanaihara et al., "Unique microRNA molecular profiles in lung cancer diagnosis and prognosis", Cancer Cell, vol. 9, Mar. 2006, pp. 189-198.
L. Garzia et al., "MicroRNA-199b-5p Impairs Cancer Stem Cells through Negative Regulation of HES1 in Medulloblastoma", PLoS ONE, vol. 4, Issue 3, Mar. 2009, pp. 1-14.
S. Pizzimenti et al., "MicroRNA expression changes during human leukemic HL-60 cell differentiation induced by 4-hydroxynonenal, a product of lipid peroxidation", Free Radical Biology & Medicine, vol. 46, 2009, pp. 282-288.
Z. Wenguang et al., "A Subset of Skin-Expressed microRNAs with Possible Roles in Goat and Sheep Hair Growth Based on Expression Profiling of Mammalian microRNAs", A Journal of Integrative Biology, vol. 11, No. 4, 2007, pp. 385-396.
A. Chao et al., "Decreased expression of microRNA-199b increases protein levels of SET (protein phosphatase 2A inhibitor) in human choriocarcinoma", Cancer Letters, vol. 291, 2010, pp. 99-107.
M. Poy et al., "*miR*-375 maintains normal pancreatic α- and β-cell mass", PNAS, vol. 106, No. 14, Apr. 7, 2009, pp. 5813-5818.
A. Ouaamari et al., "miR—375 Targets 3'-Phosphoinositide-Dependent Protein Kinase-1 and Regulates Glucose-Induced Biological Responses in Pancreatic β-Cells", Diabetes, vol. 57, Oct. 2008, pp. 2708-2717.
P. Martins et al., "MicroRNA-199b targets the nuclear kinase Dyrk1a in an auto-amplification loop promoting calcineurin/NFAT signalling", Nature Cell Biology, vol. 12, No. 12, Dec. 2010, pp. 1220-1227.

(Continued)

*Primary Examiner* — Tracy Vivlemore
*Assistant Examiner* — Kate Poliakova
(74) *Attorney, Agent, or Firm* — Wenderoth, Lind & Ponack, L.L.P.

(57) ABSTRACT

The present invention provides a prophylactic or therapeutic drug for diabetes, which contains a polynucleotide such as miR-199b* and the like. Moreover, the present invention provides a method for screening for a prophylactic or therapeutic drug for diabetes, which includes measuring an expression level of a polynucleotide such as miR-199b* and the like. Furthermore, the present invention provides a method for determining the susceptibility to a prophylactic or therapeutic drug for diabetes, which includes measuring an expression level of a polynucleotide such as miR-199b* and the like.

5 Claims, 2 Drawing Sheets

(56) References Cited

OTHER PUBLICATIONS

E. Lin et al., "miR-199a, a Bone Morphogenic Protein 2-responsive MicroRNA, Regulates Chondrogenesis via Direct Targeting to Smad1", Journal of Biological Chemistry, vol. 284, No. 17, Apr. 24, 2009, pp. 11326-11335.

S. Rane et al., "An antagonism between the AKT and beta-adrenergic signaling pathways mediated through their reciprocal effects on miR-199a-5p", Cellular Signaling, vol. 22, 2010, pp. 1054-1062.

B. Chen et al., "Identification of microRNAs expressed highly in pancreatic islet-like cell clusters differentiated from human embryonic stem cells", Cell Biology International, vol. 35, 2011, pp. 29-37.

Extended European Search Report issued Mar. 21, 2014 in corresponding Application No. 11803673.0.

Lovis et al., "Alterations in MicroRNA Expression Contribute to Fatty Acid-Induced Pancreatic β-Cell Dysfunction", Diabetes, Oct. 2008, vol. 57, No. 10, pp. 2728-2736.

Pandey et al., "MicroRNAs in Diabetes: Tiny Players in Big Disease", Cellular Physiology and Biochemistry, 2009, vol. 23, No. 4-6, pp. 221-232.

Walker, "Role of MicroRNA in Pancreatic β-Cells", Diabetes, Oct. 2008, vol. 57, No. 10, pp. 2567-2568.

\* cited by examiner

PROPHYLACTIC OR THERAPEUTIC AGENT FOR DIABETES

TECHNICAL FIELD

The present invention relates to a novel agent for the prophylaxis or treatment of diabetes. More particularly, the present invention relates to a therapeutic agent for diabetes, containing a polynucleotide such as micro RNA (hereinafter sometimes to be referred to as "miRNA") and the like, and the like.

In addition, the present invention relates to a screening method for a therapeutic drug for diabetes and the like, a method for determining the susceptibility of patients with diabetes to a therapeutic drug for diabetes and the like, and the like.

BACKGROUND OF THE INVENTION

Diabetes is one of five major diseases in the advanced countries, and its influence is increasing yearly in other countries as well. Pancreatic β cells in charge of blood glucose control are known to deal with an increase in the amount of necessary insulin in the body due to obesity, pregnancy, diabetes and the like by increasing the cell mass by hypertrophy, neogenesis, growth and apoptosis suppression. Since the current therapeutic drug for diabetes is mainly a symptomatic therapy for controlling the blood glucose level, diabetes is difficult to completely cure once it is developed. With such background, the development of a therapeutic drug for diabetes, which has a pancreatic β cell proliferation accelerating effect as a main action and aims at complete cure of diabetes, is expected.

In recent years, it is suggested that various miRNAs are expressed in animal cells and play biologically important roles. For example, miR-375 has been reported to suppress the amount of insulin secreted from pancreatic β cells in a glucose-dependent manner (non-patent document 1).

As for miR-199b*, reports have documented that the level of miR-199b-prec expression decreases in a lung cancer tissue (non-patent document 2), miR-199b-5p functions as a regulatory factor of Notch signal via the regulation of HES1 expression in a myeloma cell line (non-patent document 3), the level of miR-199b expression decreases during differentiation of human leukemia HL-60 cells by 4-hydroxynonenal (non-patent document 4), mmu-miR-199b is expressed in goat skin cells (non-patent document 5), the expression level of miR-199b is significantly low in human ciliary cancer cells as compared to normal cells (non-patent document 6) and the like. Furthermore, a diagnostic method of breast cancer by using miR-199b (patent document 1), a diagnostic method of lung cancer by using miR-199b-prec (patent document 2), a therapeutic method of cancer using hsa-mir-199a (patent document 3) and the like have been reported.

DOCUMENT LIST

Patent Documents patent document 1: WO2007/081740
patent document 2: WO2007/081720
patent document 3: WO2009/099465

Non-patent Documents non-patent document 1: Nature, 2004, 432, p. 226-230
non-patent document 2: Cancer Cell, 2006, 9, p. 189-198
non-patent document 3: PLoS ONE, 2009, 4, e4998
non-patent document 4: Free Radical Biology & Medicine, 2009, 46, p. 282-288
non-patent document 5: OMICS: A Journal of Integrative Biology, 2007, 11, p. 385-396
non-patent document 6: Cancer Letters, 2010, 291, p. 99-107

SUMMARY OF THE INVENTION

Problems to be Solved by the Invention

An object of the present invention is to provide a novel means for the prophylaxis or treatment of diabetes, having a pancreatic β cell proliferation accelerating effect as a main action. In addition, another object of the present invention is to provide a convenient and highly accurate diagnostic method for susceptibility to a prophylactic or therapeutic drug for diabetes.

Means of Solving the Problems

The present inventors have performed a comprehensive expression analysis on a pancreas tissue of a partial pancreatectomy model capable of remarkably accelerating proliferation of all pancreas cells including pancreatic β cells in the body, and further examined the proliferation accelerating effect of miRNA for pancreatic β cells in the in vitro pancreatic β cell proliferation evaluation system using the primary culture islet cells, and found that miR-199b* unexpectedly has a pancreatic β cell proliferation accelerating activity. Based on these findings, the present inventors have conducted further studies and completed the present invention.

Accordingly, the present invention relates to the following.

[1] An agent for the prophylaxis or treatment of diabetes, comprising a polynucleotide comprising a base sequence the same as or having a homology of not less than 90% to the base sequence shown by SEQ ID NO: 1, 2, 3 or 4 or a polynucleotide comprising a base sequence complementary to the base sequence, or a salt thereof.

[2] An agent for proliferating pancreatic β cells, comprising a polynucleotide comprising a base sequence the same as or having a homology of not less than 90% to the base sequence shown by SEQ ID NO: 1, 2, 3 or 4 or a polynucleotide comprising a base sequence complementary to the base sequence, or a salt thereof.

[3] A method for the prophylaxis or treatment of diabetes in a mammal, comprising administering an effective amount of a polynucleotide comprising a base sequence the same as or having a homology of not less than 90% to the base sequence shown by SEQ ID NO: 1, 2, 3 or 4 or a polynucleotide comprising a base sequence complementary to the base sequence, or a salt thereof, to said mammal.

[4] A method for proliferating pancreatic β cells in a mammal, comprising administering an effective amount of a polynucleotide comprising a base sequence the same as or having a homology of not less than 90% to the base sequence shown by SEQ ID NO: 1, 2, 3 or 4 or a polynucleotide comprising a base sequence complementary to the base sequence, or a salt thereof, to said mammal.

[5] Use of a polynucleotide comprising a base sequence the same as or having a homology of not less than 90% to the base sequence shown by SEQ ID NO: 1, 2, 3 or 4 or a polynucleotide comprising a base sequence complementary to the base sequence, or a salt thereof, for the production of an agent for the prophylaxis or treatment of diabetes.

[6] Use of a polynucleotide comprising a base sequence the same as or having a homology of not less than 90% to the base sequence shown by SEQ ID NO: 1, 2, 3 or 4 or a polynucleotide comprising a base sequence complementary to the base sequence, or a salt thereof, for the production of an agent for proliferating pancreatic β cells.

[7] A method for screening for a drug for the prophylaxis or treatment of diabetes, comprising measuring an expression level of a polynucleotide comprising a base sequence the same as or having a homology of not less than 90% to the base sequence shown by SEQ ID NO: 1, 2, 3 or 4.

[8] A method for screening for a substance that proliferates pancreatic β cells, comprising measuring an expression level of a polynucleotide comprising a base sequence the same as or having a homology of not less than 90% to the base sequence shown by SEQ ID NO: 1, 2, 3 or 4.

[9] A method for determining the susceptibility of a diabetes patient to a drug for the prophylaxis or treatment of diabetes, comprising measuring an expression level of a polynucleotide comprising a base sequence the same as or having a homology of not less than 90% to the base sequence shown by SEQ ID NO: 1, 2, 3 or 4.

[10] A method for determining the susceptibility of a diabetes patient to a pancreatic β cell proliferation drug, comprising measuring an expression level of a polynucleotide comprising a base sequence the same as or having a homology of not less than 90% to the base sequence shown by SEQ ID NO: 1, 2, 3 or 4.

Effect of the Invention

Since the polynucleotide of the present invention accelerates proliferation of pancreatic β cells, it has a prophylactic or therapeutic effect for diseases such as diabetes and the like. In addition, using the expression of the polynucleotide of the present invention as an index, screening for a prophylactic or therapeutic drug for diabetes, and determination of susceptibility to a prophylactic or therapeutic drug for diabetes can be performed.

DETAILED DESCRIPTION OF THE INVENTION

Figure 1:
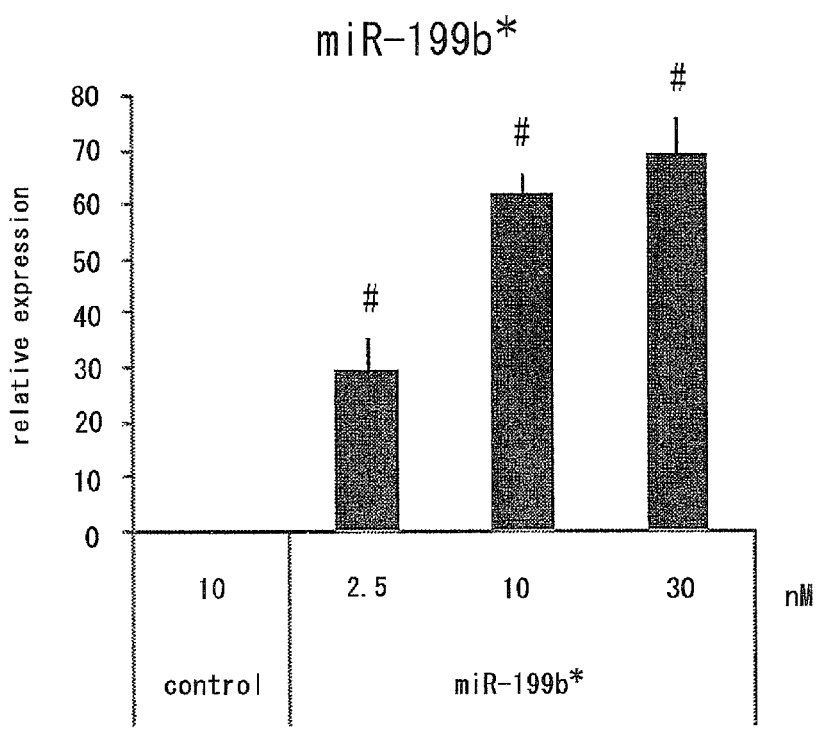
FIG. 1 shows relative expression levels of mature miR-199b* in rat primary culture islet cells transfected with Pre-miR miRNA Precursor that expresses mmu-miR-199b*. For statistical processing, parametric Williams test was used (# means significant).

In the present specification, miRNA refers to an unprocessed (e.g., precursor) or processed (for example, matured) RNA transcript produced from miRNA gene. The above-mentioned unprocessed RNA transcript is also indicated as "zenku-tai miRNA" or "precursor miRNA", and generally constituted with about 70-100 bases. The precursor miRNA is processed into an active RNA molecule having 19-25 bases by digestion with ribonuclease (e.g., Dicer), Argonaut, or ribonuclease III (e.g., *Escherichia coli* ribonuclease III). In the present specification, the active RNA molecule having 19-25 bases is referred to as "mature miRNA". The activity of mature miRNA refers to an activity to bind to a target mRNA having a sequence complementary to the mature miRNA, and causes cleavage of target mRNA.

The polynucleotide to be used in the present invention (in the present specification, sometimes to be referred to as "the polynucleotide of the present invention"), or a salt thereof contains at least one base sequence selected from the group consisting of the following (A)-(C):

(A) the base sequence shown by SEQ ID NO: 1, 2, 3 or 4;
(B) a base sequence having a homology of not less than 90% to the base sequence shown by SEQ ID NO: 1, 2, 3 or 4; and
(C) a base sequence complementary to the base sequence of the above-mentioned (A) or (B).

In the present specification, unless particularly specified, the base sequence of polynucleotide is described as a sequence of any of DNA and RNA, but thymine (T) and uracil (U) at optional positions can be deemed to be replaced with each other. In addition, when polynucleotide is DNA, it is needless to say that any uracil (U) is replaced with thymine (T), and when polynucleotide is RNA, all thymine (T) is replaced with uracil (U).

In the aforementioned (A), the base sequence shown by SEQ ID NO: 1 is a base sequence of mmu-miR-199b* (also referred to as mmu-miR-199b-5p). The base sequence shown by SEQ ID NO: 2 is mmu-miR-199b (also referred to as mmu-miR-199b-3p), which is the same base sequence as hsa-miR-199b-3p, mmu-miR-199a-3p, hsa-miR-199a-3p and rno-miR-199a-3p. The base sequence shown by SEQ ID NO: 3 is a base sequence of mmu-miR-199a-5p, hsa-miR-199a-5p and rno-miR-199a-5p. The base sequence shown by SEQ ID NO: 4 is a base sequence of hsa-miR-199b-5p.

The aforementioned base sequence (B) has a homology of not less than 90%, preferably not less than 95% (i.e., identity) to the base sequence shown by SEQ ID NO: 1, 2, 3 or 4.

As used herein, "homology" means the proportion (%) of the same base to all overlapping bases in the optimal alignment where two base sequences are aligned using a mathematic algorithm known in the relevant technical field (the algorithm is such that a gap can be introduced into one or both of the sequences for the optimal alignment). The homology of the base sequence in the present specification can be calculated, for example, using a homology calculation algorithm NCBI BLAST (National Center for Biotechnology Information Basic Local Alignment Search Tool) under the following conditions (expectancy=10; allow gap; filtering=ON; match score=1; mismatch score=−3). Other algorithms to determine the homology of a base sequence include, for example, the algorithm described in Karlin et al., Proc. Natl. Acad. Sci. USA, 90: 5873-5877 (1993) [said algorithm is incorporated in the NBLAST and XBLAST programs (version 2.0) (Altschul et al., Nucleic Acids Res., 25: 3389-3402 (1997))], the algorithm described in Needleman et al., J. Mol. Biol., 48: 444-453 (1970) [said algorithm is incorporated in the GAP program in the GCG software package], the algorithm described in Myers and Miller, CABIOS, 4: 11-17 (1988) [said algorithm is incorporated in the ALIGN program (version 2.0), which is part of the CGC sequence alignment software package], the algorithm described in Pearson et al., Proc. Natl. Acad. Sci. USA, 85: 2444-2448 (1988) [said algorithm is incorporated in the FASTA program in the GCG software package] and the like, and they can also be used preferably in the same manner.

The base sequence of the aforementioned (B) encompasses the base sequence shown by SEQ ID NO: 1, 2, 3 or 4, except that 1 or 2 bases are deleted, substituted, added or inserted. Examples of said base sequences include (i) the base sequence shown by SEQ ID NO: 1, 2, 3 or 4, except that 1 or 2 bases are deleted, (ii) the base sequence shown by SEQ ID NO: 1, 2, 3 or 4, except that 1 or 2 bases are added, (iii) the base sequence shown by SEQ ID NO: 1, 2, 3 or 4, except that 1 or 2 bases are inserted, (iv) the base sequence shown by SEQ ID NO: 1, 2, 3 or 4, except that 1 or 2 bases are substituted by another base, and (v) the base sequences wherein such mutations are combined (provided the total number of the bases deleted, substituted, added or inserted is 2).

When the base sequences contain mutations (deletion, substitution, addition or insertion) as mentioned above, there is no restriction regarding the positions of the mutations.

The base sequence of the aforementioned (C) is completely complementary to the base sequence of the above-mentioned (A) or (B). The polynucleotide of the present invention, or a salt thereof, has an activity to accelerate proliferation of pancreatic β cells. Examples of the above-mentioned pancreatic β cells include pancreatic β cells of mammals (e.g., human, monkey, mouse, rat, rabbit, swine).

The activity of the polynucleotide to accelerate proliferation of pancreatic β cells can be measured according to the method described in the below-mentioned Examples. For example, rat primary culture islet cells are transfected with an evaluation target polynucleotide at the final concentration of 2.5-50 nM by using DharmaFECT1 (Thermo Scientific) and the like, and the number of pancreatic β cells are compared on day 5 from the transfection between the group transfected with the evaluation target polynucleotide and the negative control group (group transfected with scrambled miRNA or group free of transfection with the evaluation target polynucleotide).

For example, an activity to increase the number of pancreatic β cells by 10% or more as compared to the negative control can be defined as "an activity to accelerate proliferation of pancreatic β cells".

While the length of the polynucleotide of the present invention is not particularly limited as long as it has an activity to accelerate proliferation of mammalian pancreatic β cells, from the aspects of easiness of synthesis, it is generally not more than 200 bp, preferably not more than 100 bp, more preferably not more than 80 bp.

Preferable examples of the polynucleotide of the present invention include polynucleotides containing the base sequence shown by SEQ ID NO: 1, 2, 3 or 4.

More preferable examples of the polynucleotide of the present invention include polynucleotides consisting of the base sequence shown by SEQ ID NO: 1, 2, 3 or 4.

The polynucleotide of the present invention, or a salt thereof, may be a polynucleotide containing 2-deoxy-D-ribose, a polynucleotide containing D-ribose, a polynucleotide containing N-glycoside of purine base or pyrimidine base, a polynucleotide containing non-nucleotide backbone (e.g., commercially available protein nucleic acid and synthetic sequence specific nucleic acid polymer) or other polymer containing a special bond (provided that the polymer contains a nucleotide having a configuration permitting base pairing and attachment of base as shown in DNA and RNA) and the like. These may be double-stranded DNAs, single-stranded DNAs, double-stranded RNAs, single-stranded RNAs, or DNA:RNA hybrids, and may also be unmodified polynucleotides (or unmodified oligonucleotides); polynucleotides with known modifications, for example, those with labels known in the art, those with caps, those methylated, those with substitution of one or more naturally occurring nucleotides with their analogue, those with intramolecular modifications of nucleotides such as those with uncharged linkages (for example, methyl phosphonates, phosphotriesters, phosphoramidates, carbamates and the like) and those with charged linkages or sulfur-containing linkages (for example, phosphorothioates, phosphorodithioates and the like); those having side chain groups such as proteins (nucleases, nuclease inhibitors, toxins, antibodies, signal peptides, poly-L-lysine and the like) or saccharides (for example, monosaccharides and the like); those with intercalators (for example, acridine, psoralen and the like); those with chelators (for example, metals, radioactive metals, boron, oxidative metals and the like); those with alkylating agents; or those with modified linkages (for example, a anomeric nucleic acids and the like). As used herein, "nucleotide" and "nucleic acid" may comprise not only the purine and pyrimidine bases, but also other modified heterocyclic bases. Examples of other modified heterocyclic bases include methylated purine base and pyrimidine base, and acylated purine base and pyrimidine base. The nucleotide of the present invention or a nucleoside constituting the nucleotide of the present invention may have a modified sugar moiety. Examples of the modification of the sugar moiety include substitution by a halogen atom, an aliphatic group and the like of a hydroxyl group in the sugar moiety, and conversion to a functional group such as ether, amine and the like of a hydroxyl group in the sugar moiety.

To improve the stability, the polynucleotide of the present invention may be chemically modified. Examples of such chemical modification include (a) chemical modification in the internucleoside backbone ((a-1) chemical modification of polynucleotide having a phosphorus atom in the internucleoside backbone and (a-2) chemical modification of polynucleotide without having a phosphorus atom in the internucleoside backbone), (b) chemical modification of sugar moiety, (c) modification of nucleobase moiety, (d) modification by conjugation with targeting fragments, (e) chemical modification by a polynucleotide constituting a chemically independent region, and (f) modification described in "Current protocols in nucleic acid chemistry", Beaucage, S.L. et al. (Edrs.), John Wiley & Sons, Inc., New York, N.Y., USA.

Preferable examples of the aforementioned (a-1) chemical modification of polynucleotide having a phosphorus atom in the internucleoside backbone include phosphorothioate, asymmetric phosphorothioate, phosphorodithioate, phosphotriester, aminoalkylphosphotriester, 3'-alkylenephosphonate, alkyl (e.g., methyl) phosphonate containing asymmetric phosphonate, phosphinate, 3'-aminophosphoramidate, phosphoramidate, phosphoramidate containing aminoalkyl phosphoramidate, thionophosphoramidate, thionoalkylphosphonate, thionoalkylphosphotriester, boranophosphate, 2'-5' bond analog thereof, and modification wherein the adjacent pairs of nucleoside unit is 3'-5' to 5'-3', or 2'-5' to 5'-2'.

The aforementioned (a-1) polynucleotide having a phosphorus atom in the internucleoside backbone can be produced by the methods described in, for example, U.S. Pat. Nos.

3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050 and the like, or a method analogous thereto.

Preferable examples of the aforementioned (a-2) polynucleotides without having a phosphorus atom in the internucleoside backbone include a polynucleotide having a backbone formed by an internucleoside linkage of short chain alkyl or cycloalkyl, internucleoside linkage wherein hetero atom and alkyl or cycloalkyl are mixed, or one or more short chain hetero atoms or heterocyclic internucleoside linkage. These include those having a morpholino linkage (partly formed from sugar moiety of nucleoside); siloxane backbone; sulfide, sulfoxide or sulfone backbone; formacetyl and thioformacetyl backbones; methyleneformacetyl and thioformacetyl backbones; alkene-containing backbone; sulfamate backbone; methyleneimino and methylenehydrazino backbones; sulfonate and sulfonamide backbones; amide backbone; and backbone containing a mixed part of N, O, S and $CH_2$ components.

The aforementioned (a-2) polynucleotide without having a phosphorus atom in the internucleoside backbone can be produced, for example, according to the method described in U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439 and the like, or a method analogous thereto.

Examples of the aforementioned (b) chemical modification of the sugar moiety include chemical modification for substituting the 2'-position by one substituent selected from the following group A.

group A: OH; F; O-, S-, or N-alkyl; O-, S-, or N-alkenyl; O-, S- or N-alkynyl; or O-[(alkylene)$_n$-O]$_m$-alkyl, wherein the alkyl, alkylene, alkenyl and alkynyl may be substituted or unsubstituted $C_1$ to $C_{10}$ alkyl, $C_1$ to $C_{10}$ alkylene, or $C_2$ to $C_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$O(CH$_2$)$_n$CH$_3$, O(CH$_2$)$_n$ONH$_2$, and O(CH$_2$)$_n$O(CH$_2$)$_m$NH$_2$, where n and m are from 1 to 10 (preferably 1 to 3) and NH$_2$ may be mono- or di-substituted by $C_1$ to $C_6$ alkyl (e.g. methyl). Particularly preferred chemical modification includes methoxyethoxy (—O—CH$_2$CH$_2$OCH$_3$ also known as -MOE) (Martin et al., Helv. Chim. Acta, 1995, 78, 486-504), dimethylaminooxyethoxy (—O(CH$_2$)$_2$ON(CH$_3$)$_2$ group, also known as -DMAOE), and dimethylaminoethoxyethoxy (—O—(CH$_2$)$_2$—O—(CH$_2$)$_2$—N(CH$_3$)$_2$, also known as 2'-DMAEOE).

Other examples of the aforementioned (b) chemical modification of the sugar moiety include chemical modification for substituting the 2'-position by one substituent selected from the following group B.

group B: $C_1$ to $C_{10}$ (lower alkyl, substituted lower alkyl, alkylaryl, aralkyl, O-alkylaryl or O-aralkyl), SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkylaryl, aminoalkylamino, polyalkylamino, substituted silyl, an RNA cleaving group, a reporter group, an intercalator, a group for improving the pharmacokinetic properties of polynucleotide, or a group for improving the pharmacodynamic properties of polynucleotide, and other substituents having similar properties.

Other examples of the aforementioned (b) chemical modification of the sugar moiety include chemical modification for substituting the 2'-position by methoxy, aminopropoxy or fluoro. Other examples of the chemical modification of the sugar moiety include chemical modification for substituting 3' position of sugar on 3' terminal nucleotide or sugar in 2'-5' linking polynucleotide and 5' position of 5' terminal nucleotide by methoxy, aminopropoxy or fluoro, and modification for substituting pentofuranosyl sugar by a sugar mimic such as cyclobutyl moiety.

Examples of chemical modification of other sugar moiety include modification for locking a sugar moiety as disclosed in U.S. Pat. No. 6,770,748.

Examples of chemical modification of other sugar moiety include modification for crosslinking a sugar moiety as disclosed in U.S. Pat. No. 7,217,805, WO2003/068795, WO2005/021570, U.S. Pat. No. 7,569,686, WO2009/100320, WO2007/146511, WO2007/143315, WO2007/134181 and WO2007/090071.

A polynucleotide having the above-mentioned chemical modification of sugar moiety can be produced, for example, according to the method described in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,700,920 and the like, or a method analogous thereto.

Examples of the aforementioned (c) modification of the nucleobase moiety include 5-methylcytosine (5-me-C), 5-hydroxymethyl cytosine, xanthine, hypoxanthine, 2-aminoadenine, alkyl derivatives (e.g. 6-methyl derivatives) of adenine and guanine, alkyl derivatives (e.g. 2-propyl derivatives) of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-substituted (e.g. 8-halo, 8-amino, 8-thiol, 8-thioalkyl, 8-hydroxyl) adenines and guanines, 5-substituted (e.g. 5-halo, 5-bromo, 5-trifluoromethyl) uracils and cytosines, 7-methylguanine and 7-methyladenine, 8-azaguanine and 8-azaadenine, 7-deazaguanine and 7-daazaadenine and 3-deazaguanine and 3-deazaadenine, nucleobases disclosed in U.S. Pat. No. 3,687,808, nucleobases disclosed in The Concise Encyclopedia Of Polymer Science And Engineering, pages 858-859, Kroschwitz, J. L., ed. John Wiley & Sons, 1990, nucleobases disclosed by Englisch et al., Angewandte Chemie, International Edition, 1991, 30, 613, and nucleobases disclosed by Sanghvi, Y S., Chapter 15, Antisense Research and Applications, pages 289-302, Crooke, S. T. and Lebleu, B., Ed., CRC Press, 1993.

Certain of these nucleobases are particularly useful for increasing the binding affinity of the nucleotide of the invention or salt thereof and a target mRNA.

The aforementioned (c) polynucleotide having modification of nucleobase moiety can be produced, for example, according to the method described in U.S. Pat. Nos. 3,687,808, 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,750,692 and the like, or a method analogous thereto.

Examples of the targeting fragments used for the aforementioned (d) modification by conjugation with targeting fragments include lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-S-tritylthiol (Manoharan et al., Ann. N.Y. Acad. Sci., 1992, 660, 306-309; Manoharan at al., Biorg. Med. Chem. Let., 1993, 3, 2765-2770), a thiocholesterol (Oberhauser at al., Nucl. Acids Res., 1992, 20, 533-538), an aliphatic chain, e.g., dodecandiol or undecyl residues (Saison-Behmoaras at al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan at al., Tetrahedron Lett., 1995, 36, 3651-3654; Shea at al., Nucl. Acids Res., 1990, 18, 3777-3783), a polyamine or a polyethylene glycol chain (Manoharan at al., Nucleosides & Nucleotides, 1995, 14, 969-973), or adamantane acetic acid (Manoharan at al., Tetrahedron Lett., 1995, 36, 3651-3654), a palmityl moiety (Mishra at al., Biochim. Biophys. Acta, 1995, 1264, 229-237), or an octadecylamine or hexylamino-carbonyloxycholesterol moiety (Crooke at al., J. Pharmacol. Exp. Ther., 1996, 277, 923-937).

By applying the aforementioned (d) modification by conjugation with targeting fragments to the polynucleotide of the present invention, or a salt thereof, the activity of the polynucleotide, and intracellular distribution or intracellular incorporation can be promoted.

Polynucleotide having the aforementioned (d) modification by conjugation with targeting fragments can be produced, for example, according to the method described in U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941 and the like, or a method analogous thereto.

When the polynucleotide of the present invention or a salt thereof is chemically modified, it is not necessary for all nucleosides constituting the nucleotide of the present invention or a salt thereof to be uniformly modified, and in fact the aforementioned modifications may be incorporated in single or more nucleotides or nucleoside within the inventive nucleotide or nucleosides constituting said nucleotide.

The polynucleotide of the present invention, or a salt thereof, may be simultaneously subjected to 2 or more kinds of chemical modifications.

For example, the polynucleotide of the present invention, or a salt thereof, may contain, like PNA compound (Nielsen et al., Science, 1991, 254, 1497-1500), chemical modification in both the sugar moiety and internucleoside backbone, and the polynucleotide of the present invention, or a salt thereof, having such modification shows superior binding property to target mRNA. A polynucleotide containing chemical modification in both the sugar moiety and internucleoside backbone can be produced, for example, according to the method described in U.S. Pat. Nos. 5,539,082; 5,714,331; and 5,719,262, or a method analogous thereto.

The polynucleotide of the present invention is preferably a single strand or double strand RNA (modified or non-modified RNA).

The polynucleotide of the present invention may form a salt with an inorganic base, an organic base, an inorganic acid, an organic acid and the like. Examples of the above-mentioned salts with inorganic base include alkali metal salts such as sodium salt, potassium salt; alkaline earth metal salts such as calcium salt, magnesium salt and the like; aluminum salt, ammonium salt and the like. Examples of the above-mentioned salts with organic base include salts with trimethylamine, triethylamine, pyridine, picoline, ethanolamine, diethanolamine, triethanolamine, dicyclohexylamine, N,N'-dibenzylethylenediamine. Examples of the above-mentioned salts with inorganic acid include salts with hydrochloric acid, hydrobromic acid, nitric acid, sulfuric acid, phosphoric acid. Examples of the above-mentioned salts with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid. Of these salts, a pharmacologically acceptable salt is preferable.

Preferably, when the polynucleotide of the present invention, or a salt thereof, is introduced into mammalian cells, it directly, or after being cleaved by dsRNA specific RNase such as Drosha, Dicer and the like contained in the cells, produces an active single strand RNA consisting of the above-mentioned base sequence (A) or (B). Production of such single strand RNA can be confirmed by, for example, preparing cDNA from cells using TaqMan MicroRNA Cells-to-Ct™ kit (Ambion) and the like, and subjecting the cDNA to a quantitative RT-PCR method using TaqMan miRNA assays (ABI) and the like.

The above-mentioned active single strand RNA can be obtained from a precursor miRNA by a natural processing pathway (e.g., using cell lysate), or by a synthesis processing pathway (e.g., using isolated processing enzyme such as isolated Dicer, Argonaut, ribonuclease III and the like). In addition, the above-mentioned active single strand RNA can also be produced biologically or chemically.

The polynucleotide of the present invention is more preferably a single strand RNA containing the above-mentioned base sequence (A) or (B), or a double strand RNA containing the single strand RNA as one chain.

Specific embodiments of the polynucleotide of the present invention are the following:
(1) a single strand RNA consisting of the above-mentioned base sequence (A) or (B), or a double strand RNA containing the single strand RNA as one chain;
(2) a double strand RNA containing
  a single strand RNA containing a first base sequence (one of the base sequences shown by SEQ ID NO: 1, 3 and 4, or a base sequence having a homology of not less than 90% to the base sequence), and
  a single strand RNA containing a second base sequence (one of the base sequence shown by SEQ ID NO: 2 and a base sequence having a homology of not less than 90% to the base sequence), wherein said two single strand RNAs are hybridized; (3) a single strand RNA containing the above-mentioned first base sequence and the above-mentioned second base sequence, wherein the first base sequence and the second base sequence are linked via a hairpin loop region and, in the hairpin loop structure, the first base sequence intramolecularly forms a double strand structure with the second base sequence.

Examples of the single strand RNA consisting of the base sequence (A) or (B) in the aforementioned (1) include single strand mature miR-199b and single strand mature miR-199a of mammals. Preferable examples of the single strand RNA consisting of the base sequence (A) or (B) in the aforementioned (1) include
single strand RNA consisting of the base sequence shown by SEQ ID NO: 1 (mmu-miR-199b* (also referred to as mmu-miR-199b-5p)), single strand RNA consisting of the base sequence shown by SEQ ID NO: 2 (mmu-miR-199b (also referred to as mmu-miR-199b-3p, hsa-miR-199b-3p, mmu-miR-199a-3p, hsa-miR-199a-3p or rno-miR-199a-3p)), single strand RNA consisting of the base sequence shown by SEQ ID NO: 3 (mmu-miR-199a-5p (also referred to as hsa-miR-199a-5p or rno-miR-199a-5p)), and single strand RNA consisting of the base sequence shown by SEQ ID NO: 4 (hsa-miR-199b-5p).

The double strand RNA of the aforementioned (2) contains a single strand RNA having a homology of not less than 90%, preferably not less than 95%, to the base sequence shown by SEQ ID NO: 1, 3 or 4. The double strand RNA of the aforementioned (2) contains a single strand RNA having a homology of not less than 90%, preferably not less than 95%, to the base sequence shown by SEQ ID NO: 2.

The RNA of the aforementioned (2) is representatively RNA containing miR-199b or miR-199a of a mammal. Specifically, RNA containing a single strand RNA consisting of the base sequence shown by SEQ ID NO: 1 (mmu-miR-199b*) and a single strand RNA consisting of the base sequence shown by SEQ ID NO: 2 (mmu-miR-199b), RNA containing a single strand RNA consisting of the base sequence shown by SEQ ID NO: 4 (hsa-miR-199b-5p) and a single strand RNA consisting of the base sequence shown by SEQ ID NO: 2 (mmu-miR-199b), RNA containing a single strand RNA consisting of the base sequence shown by SEQ ID NO: 3 (mmu-miR-199a-5p) and a single strand RNA consisting of the base sequence shown by SEQ ID NO: 2 (mmu-miR-199b), and the like can be mentioned.

In the aforementioned (3), the length of the hairpin loop region is not particularly limited as long as RNA has an activity to accelerate proliferation of mammalian pancreatic β cells. It is generally about 5-25 bases. The base sequence of the hairpin loop region is not particularly limited as long as it can form a loop and RNA has an activity to accelerate proliferation of mammalian pancreatic β cells.

As RNA of the aforementioned (3), representatively, precursor miRNA and primary transcript of mammalian miR-199b or miR-199a, a single strand RNA containing a base sequence of these RNAs and the like can be mentioned. Specifically, single strand RNA consisting of the base sequence shown by SEQ ID NO: 5 (precursor mmu-miR-199b), single strand RNA consisting of the base sequence shown by SEQ ID NO: 6 (precursor hsa-miR-199b), single strand RNA consisting of the base sequence shown by SEQ ID NO: 7 or SEQ ID NO: 8 (precursor mmu-miR-199a), single strand RNA consisting of the base sequence shown by SEQ ID NO: 9 or SEQ ID NO: 10 (precursor hsa-miR-199a), single strand RNA consisting of the base sequence shown by SEQ ID NO: 11 (primary transcript of mmu-miR-199b), single strand RNA consisting of the base sequence shown by SEQ ID NO: 12 (primary transcript of hsa-miR-199b), single strand RNA consisting of the base sequence shown by SEQ ID NO: 13 or SEQ ID NO: 14 (primary transcript of mmu-miR-199a), single strand RNA consisting of the base sequence shown by SEQ ID NO: 15 or SEQ ID NO: 16 (primary transcript of hsa-miR-199a), single strand RNA containing any of the base sequences shown by SEQ ID NOs: 5-16 and the like can be mentioned.

The NCBI accession Nos. of miRNAs shown by SEQ ID NO: 1 to 10 are as described below.

mmu-miR-199b*: SEQ ID NO: 1 (MIMAT0000672)
mmu-miR-199b: SEQ ID NO: 2 (MIMAT0004667)
mmu-miR-199a-5p: SEQ ID NO: 3 (MIMAT0000229)
hsa-miR-199b-5p: SEQ ID NO: 4 (MIMAT0000263)
precursor mmu-miR-199b: SEQ ID NO: 5 (MI0000714)
precursor hsa-miR-199b: SEQ ID NO: 6 (MI0000282)
precursor mmu-miR-199a: SEQ ID NO: 7 (MI0000241)
precursor mmu-miR-199a: SEQ ID NO: 8 (MI0000713)
precursor hsa-miR-199a: SEQ ID NO: 9 (MI0000242)
precursor hsa-miR-199a: SEQ ID NO: 10 (MI0000281)

The base sequence shown by the aforementioned SEQ ID NO: 2 is also referred to as mmu-miR-199b-3p and is the same as mmu-miR-199a-3p (NCBI accession No. MIMAT0000230), hsa-miR-199a-3p (NCBI accession No. MIMAT0000232) and hsa-miR-199b-3p (NCBI accession No. MIMAT0004563).

The base sequence shown by the aforementioned SEQ ID NO: 3 is the same as hsa-miR-199a-5p (NCBI accession No. MIMAT0000231) and rno-miR-199a-5p.

The polynucleotide of the present invention, or a salt thereof, can be synthesized based on the sequence information disclosed in the present specification or known database and using a commercially available automated DNA/RNA synthesizer (Applied Biosystems, Beckman and the like). In addition, double strand polynucleotides can be prepared by separately synthesizing both strands using an automated DNA/RNA synthesizer, and denaturing the strands in an appropriate annealing buffer solution at about 90° C. to about 95° C. for about 1 minute, and then annealing at about 30° C. to 70° C. for about 1 to about 8 hours. A longer double-stranded polynucleotide can also be prepared by synthesizing complementary oligonucleotide strands in a way such that they overlap with each other, annealing these strands, and then performing ligation with a ligase.

In addition, an expression vector for expressing the above-mentioned polynucleotide of the present invention (hereinafter, sometimes to be referred to as "the expression vector of the present invention") is also one preferable embodiment of the polynucleotide of the present invention. The expression vector of the present invention is constituted such that the polynucleotide of the present invention mentioned above can be expressed in mammalian cells. The expression vector of the present invention can be produced by ligating the polynucleotide of the present invention mentioned above, or a DNA encoding same to the downstream of the promoter in a suitable expression vector.

Examples of the expression vectors include, but are not limited to, *Escherichia coli*-derived plasmid (e.g., pBR322, pBR325, pUC12, pUC13), *Bacillus subtilis*-derived plasmid (e.g., pUB110, pTP5, pC194), yeast-derived plasmid (e.g., pSH19, pSH15), bacteriophage such as λ phage and the like, animal virus such as retrovirus, vaccinia virus, baculovirus etc., and the like, as well as pA1-11, pXT1, pRc/CMV, pRc/RSV and pcDNAI/Neo.

The promoter may be any as long as it is functionable in mammalian cells. Examples of the promoters include pol II-promoters and pol III-promoters. Examples of the Pol III-promoters include U6 promoter, H1 promoter, 5SrRNA promoter, tRNA promoter, 7SL promoter, 7SK promoter, retrovirus LTR promoter, and adenovirus Val promoter. Of these, U6 promoter, H1 promoter or tRNA promoter is preferable. Examples of the pol II-promoters include insulin promoter, cytomegalovirus promoter, T7 promoter, T3 promoter, SP6 promoter, RSV promoter, EF-1a promoter, β-actin promoter, γ-globulin promoter, and SRα promoter. Of these, insulin promoter is preferable.

As the expression vectors, in addition to the above, those optionally harboring an enhancer, a splicing signal, a poly A addition signal, a selection marker, an SV40 replication origin (hereinafter also abbreviated as SV40ori) and the like. As examples of the selection markers, the dihydrofolate reductase (hereinafter also abbreviated as dhfr) gene [methotrexate (MTX) resistance], the ampicillin resistance gene (hereinafter also abbreviated as Amp$^r$), the neomycin resistance gene (hereinafter also abbreviated as Neo$^r$, G418 resistance) and the like can be used.

The above-mentioned polynucleotide of the present invention, or a salt thereof, has, for example, the following uses.
<1> use as a prophylactic or therapeutic drug for diabetes,
<2> use as an agent for proliferating pancreatic β cells,
<3> use for screening for a prophylactic or therapeutic drug for diabetes and the like,
<4> use for determining susceptibility to a prophylactic or therapeutic drug for diabetes and the like.

<1> Use as prophylactic or therapeutic drug for diabetes

As shown in the below-mentioned Examples, the polynucleotide of the present invention, or a salt thereof, has an activity to accelerate proliferation of pancreatic β cells. Such fact shows that administration of the polynucleotide of the present invention, or a salt thereof, to patients with diabetes and the like can accelerate proliferation of pancreatic β cells in said patients, and can prevent or treat diseases such as diabetes and the like, and the polynucleotide of the present invention, or a salt thereof, is useful as a medicament.

Therefore, the polynucleotide of the present invention, or a salt thereof, can be used as a medicament such as an agent for the prophylaxis or treatment of diabetes (e.g., type 1 diabetes, type 2 diabetes, gestational diabetes, obese diabetes); an agent for the prophylaxis or treatment of impaired glucose tolerance (IGT); an agent for preventing progression from impaired glucose tolerance to diabetes and the like.

The polynucleotide of the present invention or a salt thereof targets genes such as MLK3, FGF7, Ptprf, RB1 and Serpine2 (particularly, MLK3 and FGF7), and is considered to possibly accelerate proliferation of pancreatic β cells by suppressing expression of these genes, and prevent or treat diseases such as diabetes and the like. Therefore, an inhibitor of MLK3, FGF7, Ptprf, RB1 and Serpine2 (particularly, MLK3 and FGF7) (e.g., low-molecular-weight compound, neutralizing antibody, siRNA, antisense nucleic acid) can also be used as a medicament such as an agent for the prophylaxis or treatment of diabetes (e.g., type 1 diabetes, type 2 diabetes, gestational diabetes, obese diabetes); an agent for the prophylaxis or treatment of impaired glucose tolerance (IGT); an agent for suppressing progression from impaired glucose tolerance to diabetes and the like.

As for diagnostic criteria of diabetes, according to the report by the Japan Diabetes Society, diabetes mellitus is a condition wherein the fasting blood glucose level (glucose concentration in venous plasma) is not less than 126 mg/dl, the 2-hour value (glucose concentration in venous plasma) of the 75 g oral glucose tolerance test (75 g OGTT) is not less than 200 mg/dl or the casual blood glucose level (glucose concentration in venous plasma) is not less than 200 mg/dl. In addition, a condition that does not fall within the scope of the above definition of diabetes mellitus, and which is not a "condition wherein the fasting blood glucose level (glucose concentration in venous plasma) is less than 110 mg/dl or the 2-hour value (glucose concentration in venous plasma) of the 75 g oral glucose tolerance test (75 g OGTT) is less than 140 mg/dl" (normal type), is called the "borderline type".

According to the reports by ADA and WHO, diabetes mellitus is a condition where the fasting blood glucose level (glucose concentration in venous plasma) is not less than 126 mg/dl, and the 2-hour value (glucose concentration in venous plasma) of the 75 g oral glucose tolerance test is not less than 200 mg/dl.

In addition, according to the above reports by ADA and WHO, impaired glucose tolerance is a condition where the 2-hour value (glucose concentration in venous plasma) of the 75 g oral glucose tolerance test is not less than 140 mg/dl and less than 200 mg/dl. Furthermore, according to the ADA report, a condition where the fasting blood glucose level (glucose concentration in venous plasma) is not less than 100 mg/dl and less than 126 mg/dl, is called IFG (Impaired Fasting Glucose). On the other hand, according to the WHO report, a condition of IFG (Impaired Fasting Glucose) as such, where the fasting blood glucose level (glucose concentration in venous plasma) is not less than 110 mg/dl and less than 126 mg/dl, is called IFG (Impaired Fasting Glycemia).

The polynucleotide of the present invention, or a salt thereof, is also used as an agent for the prophylaxis or treatment of diabetes determined by the above-mentioned diagnostic criteria, borderline type, impaired glucose tolerance, IFG (Impaired Fasting Glucose) and IFG (Impaired Fasting Glycaemia). Furthermore, the compound of the present invention can prevent progression from borderline type, impaired glucose tolerance, IFG (Impaired Fasting Glucose) or IFG (Impaired Fasting Glycaemia) to diabetes.

The polynucleotide of the present invention, or a salt thereof, can also be used, for example, as an agent for the prophylaxis or treatment of diabetic complications [e.g., neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia hypacusis, hypacusis, cerebrovascular disorder, peripheral blood circulation disorder], diabetic cachexia, insulin resistance syndrome and the like.

The polynucleotide of the present invention or a salt thereof can be administered, as a medicament (sometimes to be abbreviated as "the medicament of the present invention"), orally or parenterally as it is or in a mixture with a pharmacologically acceptable carrier.

In another embodiment, moreover, the polynucleotide of the present invention, or a salt thereof, can be formulated into a biological preparation, a liposome preparation, an emulsion or a microemulsion preparation.

The medicament of the present invention can be produced using a production method known per se, which is generally used in the technical field of preparations (e.g., the method described in the Japanese Pharmacopoeia). In this case, additives such as excipient, binder, disintegrant, lubricant, sweetening agent, surfactant, suspending agent, emulsifier, dispersing agent, thickener, diluent, penetration enhancer, a composition for complexing the polynucleotide of the present invention or a salt thereof and the like; topical delivery agent and the like, which are generally used in the technical field of preparations, can be appropriately added in suitable amounts, where necessary.

Examples of the dosage forms of the medicament of the present invention for oral administration of the polynucleotide of the present invention or a salt thereof include oral preparations such as tablet (including sugar-coated tablet, film-coated tablet, sublingual tablet, buccal tablet, mouth cavity quick-integrating tablet), pill, granule, powder, capsule (including soft capsule, microcapsule), syrup, emulsion, suspension and films (e.g., mouth cavity mucous membrane adhesion film), powder, microgranule, nanogranule, gel capsule, spray and the like.

In one embodiment, the medicament of the present invention is an oral preparation to be administered in combination with one or more penetration enhancers.

Preferable examples of the penetration enhancers include fatty acid or an ester or a salt thereof; and bile acid or a salt thereof.

Preferred bile acids or a salt thereof include chenodeoxycholic acid (CDCA), ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, glycodihydrofusidic acid or a pharmaceutically acceptable salt (e.g. sodium salt) thereof. Preferred fatty acids or an ester or a salt thereof include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, a monoglyceride, a diglyceride, polyoxyethylene-9-lauryl ether, polyoxyethylene-20-cetyl ether or a pharmaceutically acceptable salt thereof (e.g. sodium).

In some embodiments, combinations of penetration enhancers (e.g. a fatty acid or a salt thereof in combination with a bile acid or a salt thereof) can be used. A preferred combination is the sodium salts of lauric acid, capric acid and UDCA.

When the polynucleotide of the present invention, or a salt thereof, is prepared into a tablet, for example, it can be prepared by using an excipient, a binder, a disintegrant, a lubricant and the like, and when a pill or a granule is to be prepared, it can be prepared by using an excipient, a binder or a disintegrant. When a powder or a capsule is to be prepared, it can be prepared by using an excipient and the like, when a syrup is to be prepared, it can be prepared by using a sweetener and the like, and when an emulsion or a suspension is to be prepared, it can be prepared by using a suspending agent, a surfactant, an emulsifier and the like.

Examples of the excipients include lactose, sucrose, glucose, starch, sucrose, microcrystalline cellulose, powdered glycyrrhiza, mannitol, sodium hydrogen carbonate, calcium phosphate and calcium sulfate.

Examples of the binders include 5-10 wt % starch liquid paste, 10-20 wt % gum arabic solution or gelatin solution, 1-5 wt % tragacanth solution, carboxymethyl cellulose solution, sodium alginate solution and glycerin.

Examples of the disintegrants include starch and calcium carbonate.

Examples of the lubricants include magnesium stearate, stearic acid, calcium stearate and purified talc.

Examples of the sweeteners include glucose, fructose, invert sugar, sorbitol, xylitol, glycerin and simple syrup.

Examples of the surfactants include sodium lauryl sulfate, polysorbate 80, sorbitan monofatty acid ester and polyoxyl 40 stearate.

Examples of the suspending agents include gum arabic, sodium alginate, sodium carboxymethyl cellulose, methyl cellulose and bentonite.

Examples of the emulsifiers include gum arabic, tragacanth, gelatin, polysorbate 80 and the like.

When the polynucleotide of the present invention, or a salt thereof, is produced as granules or spray, a composition for complexing the polynucleotide of the present invention, or a salt thereof, and the like can be used. Examples of the compositions include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches;

polyalkylcyanoacrylates; DEAE-derivatized polyimines, pollulans, celluloses and starches. Preferable examples of the compositions include chitosan, N-trimethylchitosan, poly-L-lysine, polyhistidine, polyornithine, polyspermines, protamine, polyvinylpyridine, polythiodiethylaminomethylethylene P(TDAE), polyamino(e.g., p-amino) styrene, polymethylcyanoacrylate, polyethylcyanoacrylate, polybutylcyanoacrylate, polyisobutylcyanoacrylate, polyisohexylcynaoacrylate, DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG).

An oral preparation containing the polynucleotide of the present invention can be produced according to the methods described in U.S. Pat. No. 6,887,906, US-A-2003/0027780, U.S. Pat. No. 6,747,014 and the like, or a method analogous thereto.

Examples of the dosage forms for parenteral administration of the polynucleotide of the present invention or salt thereof include injection, injection, instillation, suppository, transdermal patch, ointment, lotion, cream, drop, spray and powder. In addition, a sustained release preparation can be made by combining the polynucleotide of the present invention, or a salt thereof, with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester).

Examples of the injection methods include intravenous injection as well as subcutaneous injection, intracutaneous injection, intramuscular injection, instillation and the like. Examples of the sustained release preparations include an iontophoresis transdermal agent and the like.

Such injections are prepared by methods known per se, or by dissolving, suspending or emulsifying the nucleotide of the present invention or a salt thereof in a sterilized aqueous or oily liquid. Examples of the aqueous liquids for injection include physiological saline, isotonic solutions containing glucose or other auxiliary drugs (e.g., D-sorbitol, D-mannitol, sodium chloride and the like) and the like, and they can be used in combination with suitable solubilizing agents such as alcohols (e.g., ethanol), polyalcohols (e.g., propylene glycol, polyethylene glycol) and nonionic surfactants (e.g., polysorbate 80, HCO-50). Examples of the oily liquids include sesame oil, soybean oil and the like and they can be used in combination with solubilizing agents such as benzyl benzoate and benzyl alcohol. In addition, buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol) and the like can be blended. A prepared injection is generally filled in an ampoule.

In one embodiment, the medicament of the present invention can be formulated as an injection.

The injection may contain a sterilized aqueous solution or an aqueous solution containing buffering agent, diluent and other appropriate additives (e.g., penetration enhancer, carrier compound and other pharmaceutically acceptable carrier or excipient, etc.) in sterilized aqueous solution.

The injection can also be used for topical administration (intrapancreas administration).

When the medicament of the present invention is formulated in a dosage form for topical administration (suppository, transdermal patch, ointment, lotion, cream, drop, spray, powder etc.), a topical delivery agent can be used.

Examples of the topical delivery agents include liposomes constituted by lipids (e.g. dioleoylphosphatidyl DOPE ethanolamine, dimyristoylphosphatidylcholine DMPC, distearolyphosphatidylcholine, dimyristoylphosphatidylglycerol DMPG, dioleoyltetramethylaminopropyl DOTAP and dioleoylphosphatidylethanolamine DOTMA, phosphatidylcholine, dimyristoylphosphatidylcholine, dipalmitoylphosphatidylcholine, dimyristoylphosphatidylglycerol or dioleoylphosphatidylethanolamine), fatty acids and fatty acid esters (e.g. arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g., isopropylmyristate IPM), monoglyceride, diglyceride or pharmaceutically acceptable salt thereof) and the like, commercially available liposomes (Lipofectin™ (Invitrogen/Life Technologies, Carlsbad, Calif.) and Effectene™ (Qiagen, Valencia, Calif.)), liposomes described in Nature Biotechnology, 15: 647-652 (1997), liposome described in J. Am Soc. Nephrol. 7: 1728 (1996), liposomes described in U.S. Pat. No. 6,271,359, liposomes described in PCT Publication WO 96/40964 and liposomes described in Nat Biotechnol. 23:1002-1007 (2005). The term "liposome" used in the present invention means a vesicle composed of amphiphilic lipids arranged in a spherical bilayer or bilayers, and includes monolayers, micelles, bilayers and vesicles.

The polynucleotide of the present invention or salt thereof may be encapsulated within liposomes or may form complexes thereto, in particular to cationic liposomes. Alternatively, the polynucleotide of the present invention or salt thereof may be complexed to lipids, in particular to cationic lipids.

A preparation for topical administration can be produced according to, for example, the method described in U.S. Pat. No. 6,747,014 and the like, or a method analogous thereto.

Examples of the liposomes to be used for formulation of the medicament of the present invention as a liposome preparation include (aa) cationic liposomes, (bb) anionic liposomes, (cc) nonionic liposomes, (dd) "sterically stabilized" liposomes, (ee) liposomes comprising glycolipids, (ff) liposomes comprising lipids derivatized with hydrophilic polymers, (gg) transfersomes, and (hh) SNALPs.

Examples of the above-mentioned (aa) cationic liposomes include liposomes used in Biochem. Biophys. Res. Commun., 1987, 147, 980-985.

Examples of the above-mentioned (cc) nonionic liposomes include Novasome™ I (glyceryl dilaurate/cholesterol/polyoxyethylene-10-stearyl ether) and Novasome™ II (glyceryl distearate/cholesterol/polyoxyethylene-10-stearyl ether) (Hu et al. S.T.P. Pharma. Sci., 1994, 4, 6, 466).

Examples of the above-mentioned (dd) "sterically stabilized" liposomes are those in which part of the vesicle-forming lipid portion of the liposome (dd-1) comprises one or more glycolipids, such as monosialoganglioside $G_{M1}$, or (dd-2) is derivatized with one or more hydrophilic polymers, such as a polyethylene glycol (PEG) moiety.

The liposome is advantageous in that it extends the period when the medicament of the present invention is present in the circulating blood.

Examples of the above-mentioned (ee) liposomes comprising glycolipids include (ee-1) liposomes comprising monosialoganglioside $G_{M1}$, galactocerebroside sulfate and phosphatidylinositol, and (ee-2) liposomes comprising sphingomyelin, ganglioside $G_{M1}$ or a galactocerebroside sulfate ester (U.S. Pat. No. 4,837,028 and WO 88/04924).

With use of these liposomes, blood half-lives of liposomes can be prolonged (Ann. N.Y. Acad. Sci., 1987, 507, 64; Proc. Natl. Acad. Sci. U.S.A., 1988, 85, 6949).

Examples of the above-mentioned (ff) liposomes comprising lipids derivatized with hydrophilic polymers include (ff-1) liposomes comprising a nonionic detergent that contains a PEG moiety (Bull. Chem. Soc. Jpn., 1980, 53, 2778), (ff-2) liposomes derivatized with hydrophilic polymeric glycols of polystyrene particles (FEBS Lett., 1984, 167, 79), (ff-3) liposomes comprising synthetic phospholipids modified by the attachment of carboxylic groups of polyalkylene glycols (e.g., PEG) (U.S. Pat. Nos. 4,426,330 and 4,534,899), (ff-4) liposomes comprising phosphatidylethanolamine (PE) derivatized with PEG or PEG stearate (FEBS Lett., 1990, 268, 235), (ff-5) liposomes comprising other PEG-derivatized phospholipids formed from the combination of distearoylphosphatidylethanolamine (DSPE) and PEG (Biochimica et Biophysica Acta, 1990, 1029, 91), (ff-6) liposomes having covalently bound PEG moieties on their external surface (European Patent No. EP 0 445 131 B1 and WO 90/04384), (ff-7) liposomes containing 1-20 mole percent of PE derivatized with PEG (U.S. Pat. Nos. 5,013,556 and 5,356,633, U.S. Pat. No. 5,213,804 and European Patent No. EP 0 496 813 B1, (ff-8) liposomes comprising a number of other lipid-polymer conjugates (WO 91/05545, U.S. Pat. No. 5,225,212 and WO 94/20073), (ff-9) liposomes comprising PEG-modified ceramide lipids (WO 96/10391), and (ff-10) PEG-containing liposomes that can be further derivatized with functional moieties on their surfaces (U.S. Pat. No. 5,540,935 and U.S. Pat. No. 5,556,948).

Liposomes comprising PEG can be prepared according to the methods described in U.S. Pat. Nos. 6,049,094; 6,224,903; 6,270,806; 6,471,326; 6,958,241 and the like, or a method analogous thereto.

Examples of the above-mentioned (hh) SNALPs include SPLP (including pSPLP (WO 00/03683) and SNALP. SNALP and SPLP can further contain a cationic lipid, a non-cationic lipid and, optionally, a lipid that prevents aggregation of particle (e.g., PEG-lipid conjugate).

The medicament of the present invention formulated into a preparation containing SNALPs is useful for systemic administration, since it advantageously extends circulation lifetime after intravenous (i.v.) injection and it is accumulated at a distal site (e.g., site physically far from the administration site).

Preparations containing SNALPs can be produced according to the methods described in, for example, U.S. Pat. Nos. 5,976,567; 5,981,501; 6,534,484; 6,586,410; 6,815,432; and WO96/40964 and the like, or a method analogous thereto.

The above-mentioned liposome preparations include monolayers, micelles, bilayers and vesicles. The "liposome" used in the present invention is composed of amphiphilic lipids arranged in a spherical bilayer or bilayers.

Examples of the above-mentioned amphiphilic lipids include cationic lipids having a pKa of from 4 to 15, comprising at lease one protonatable group (e.g. N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLendMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA), 2,2-Dilinoleyl-4-dimethylaminoethyl-[1,3]-dioxolane, or analogs thereof, or a mixture thereof), a lipid represented by the formula:

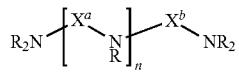

wherein
$X^a$ and $X^b$ are each independently $C_{1-6}$ alkylene;
n is 0, 1, 2, 3, 4, or 5;
each R is independently H,

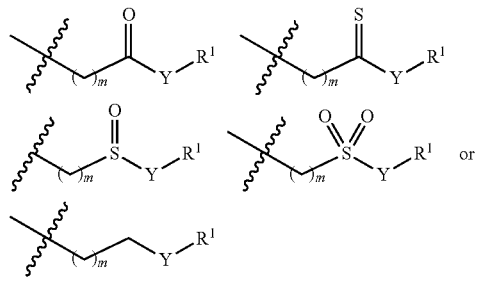

m is 0, 1, 2, 3 or 4;
Y is absent, 0, $NR^2$, or S;
$R^1$ is alkyl alkenyl or alkynyl; each of which is optionally substituted by one or more substituents; and
$R^2$ is H, alkyl, alkenyl or alkynyl; each of which is optionally substituted by one or more substituents.

Other examples of the amphiphilic lipids include non-cationic lipids (anionic lipids or neutral lipids) (e.g. distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), 1-2-distearoyl-sn-glycelo-3-phosphocholine, cholesterol, or a mixture thereof).

Further examples of the amphiphilic lipids include a polyethyleneglycol (PEG)-lipid including a PEG-diacylglycerol (DAG), a PEG-dialkyloxypropyl (DAA) (e.g. a PEG-dilauryloxypropyl (C12), a PEG-dimyristyloxypropyl (C14), a PEG-dipalmityloxypropyl (C16), a PEG-distearyloxypropyl (C18)), a PEG-phospholipid, a PEG-ceramide (Cer), and a mixture thereof.

Liposome preparations may contain a lipid that prevents aggregation of particles (e.g. steroid such as cholesterol).

Advantages of forming the medicament of the present invention as a liposome preparation are as follows: liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245); increased accumulation of the polynucleotide of the present invention or a salt thereof at the desired target; the ability to administer a wide variety of drugs, both hydrophilic and hydrophobic, into the skin.

The medicament of the present invention can be formulated as an emulsion.

The above-mentioned emulsifiers may contain surfactants, naturally occurring emulsifiers, absorption bases, finely dispersed solids, preservatives, antioxidants and the like (Idson, in Pharmaceutical Dosage Forms, Lieberman, Rieger and Banker (Eds.), 1988, Marcel Dekker, Inc., New York, N.Y., volume 1, p. 199).

As the above-mentioned surfactants, publicly known surfactants can be used (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199).

Examples of the above-mentioned naturally occurring emulsifiers include lanolin, beeswax, phosphatides, lecithin and acacia.

Examples of the above-mentioned preservatives include methyl paraben, propyl paraben, quaternary ammonium salts, benzalkonium chloride, esters of p-hydroxybenzoic acid, and boric acid.

Examples of the above-mentioned antioxidants include radical scavengers such as tocopherols, alkyl gallates, butylated hydroxyanisole, butylated hydroxytoluene; reducing agents such as ascorbic acid and sodium metabisulfite; citric acid, tartaric acid; and lecithin.

The application of emulsion formulations via dermatological, oral and parenteral routes and methods for their manufacture have been reported in the literatures (Idson, in Pharmaceutical Dosage Forms, Lieberman, Rieger and Banker (Eds.), 1988, Marcel Dekker, Inc., New York, N.Y., volume 1, p. 199).

Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199).

The medicament of the present invention may by formulated as microemulsions.

The above-mentioned microemulsions may contain oils, water, surfactants, cosurfactants and/or electrolytes.

Examples of the above-mentioned surfactants include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (P0500), decaglycerol monocaprate (MCA750), decaglycerol monooleate (MO750), decaglycerol sequioleate (SO750), decaglycerol decaoleate (DAO750), alone or in combination with cosurfactants. Examples of the above-mentioned cosurfactants include a short-chain alcohol such as ethanol, 1-propanol, and 1-butanol. Cosurfactants penetrate into the surfactant film and consequently create a disordered film because of the void space generated among surfactant molecules. The film serves to increase the interfacial fluidity. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The above-mentioned oils include Captex 300, Captex 355, Capmul MCM, fatty acid esters, medium chain ($C_8$-$C_{12}$) mono, di, and triglycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are prepared by first dispersing an oil in an aqueous surfactant solution and then adding an intermediate chain-length alcohol and the like to form a transparent system.

Microemulsions are efficient from the standpoint of the solubilization of the polynucleotide of the present invention or a salt thereof and the enhanced absorption of the polynucleotide of the present invention or a salt thereof (Constantinides et al., Pharmaceutical Research, 1994, 11, 1385-1390; Ritschel, Meth. Find. Exp. Clin. Pharmacol., 1993, 13, 205). In addition, microemulsions are effective from the standpoints of easier oral administration than solid dosage forms, superior clinical potency, and decreased toxicity (Constantinides et al., Pharmaceutical Research, 1994, 11, 1385; Ho et al., J. Pharm. Sci., 1996, 85, 138-143).

In one embodiment of the medicament of the present invention, the ratio (mass/mass ratio) of lipid to polynucleotide is within the range of about 1:1-about 50:1, about 1:1-about 25:1, about 3:1-about 15:1, about 4:1-about 10:1, about 5:1-about 9:1, or about 6:1-about 9:1.

While the content of the polynucleotide of the present invention, or a salt thereof, in the medicament of the present invention varies depending on the form of the preparation, it is generally not less than about 0.01 wt % and less than 100 wt %, preferably about 2 to about 85 wt %, more preferably about 5 to about 70 wt %, relative to the whole preparation.

While the content of the additive in the medicament of the present invention varies depending on the form of the preparation, it is generally about 1 to about 99.9 wt %, preferably about 10 to about 90 wt %, relative to the whole preparation.

The polynucleotide of the present invention can also be delivered to the target cells or target tissues by a biological method.

While the above-mentioned target cells are not particularly limited as long as they are mammalian cells (e.g., human, mouse, rat, rabbit, sheep, swine, bovine, cat, dog, monkey) that naturally express the polynucleotide of the present invention, for example, human cell can be used. Examples of the above-mentioned target tissues include pancreatic islet containing pancreatic β cells, pancreas, lung, bladder, placenta, mammary gland, and colon.

While the above-mentioned biological method includes use of a viral vector, various methods, which are not limited thereby, can be used.

The polynucleotide of the present invention is delivered using, for example, a viral vector (e.g., adenovirus and herpes virus vector) to liver cells and pancreas cells.

The viral vector that expresses the polynucleotide of the present invention can be produced by a standard molecular biological technique.

The polynucleotide of the present invention, or a salt thereof, is stable and low toxic, and can be safely administered to mammals (e.g., human, mouse, rat, rabbit, sheep, swine, bovine, cat, dog, monkey). While the daily dose varies depending on the condition and body weight of patients, the kind of polynucleotide, administration route and the like, when orally administered to patients for the treatment of diabetes, for example, the dose for an adult human (body weight about 60 kg) per day is about 1 to about 1000 mg, preferably about 3 to about 300 mg, more preferably about 10 to about 200 mg, as an active ingredient (polynucleotide of the present invention), and the dose can be administered once or in 2 or 3 portions.

When the polynucleotide of the present invention, or a salt thereof, is parenterally administered, it is generally administered in a liquid form (e.g., injection). While the single dose varies depending on the administration subject, target organ, symptom, administration method and the like, it is conveniently administered in the form of, for example, an injection at generally about 0.01 to about 100 mg, preferably about 0.01 to about 50 mg, more preferably about 0.01 to about 20 mg, per kg body weight by intravenous injection.

The polynucleotide of the present invention or a salt thereof can be used in combination with other drugs, specifically, other agent for the prophylaxis or treatment of diabetes, or a drug for proliferating pancreatic β cells.

Examples of the prophylactic or therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO 2007/013694, WO 2007/018314, WO 2008/093639 or WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g. sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compounds described in WO 2004/041266, WO 2004/106276, WO 2005/063729, WO 2005/063725, WO 2005/087710, WO 2005/095338, WO 2007/013689 or WO 2008/001931), GLP-1 receptor agonists (e.g., GLP-1, GLP-1MR, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP-355, compounds described in WO 2006/112549, WO 2007/028135, WO 2008/047821, WO 2008/050821, WO 2008/136428 or WO 2008/156757), GIP (Glucose-dependent insulinotropic peptide), GPR119 agonist (e.g. PSN821), FGF21, FGF analogues and the like.

Examples of the drugs for proliferating pancreatic β cells include dipeptidyl peptidase IV inhibitors (e.g., Alogliptin or a salt thereof (preferably benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), GLP-1 receptor agonists (e.g., GLP-1, GLP-1MR, Liraglutide, Exenatide, AVE-0010, BIM-51077, Aib(8,35)hGLP-1(7,37)NH$_2$, CJC-1131, Albiglutide) growth hormones and the like.

<2> Use as an Agent for Proliferating Pancreatic β Cells

The polynucleotide of the present invention, or a salt thereof, has an activity to accelerate proliferation of pancreatic β cells. Examples of the above-mentioned pancreatic β cells include pancreatic β cells of mammals (e.g., mouse, rat, hamster, rabbit, cat, dog, bovine, sheep, monkey, human).

Therefore, the polynucleotide of the present invention, or a salt thereof, is useful as an agent for proliferating mammalian pancreatic β cells of a; an agent for proliferating pancreatic β cells before islet transplantation; an agent for aiding proliferation of pancreatic β cells after islet transplantation; and a therapeutic agent for pancreatitis.

The activity of polynucleotide to proliferate pancreatic β cells can be measured by the method described in detail in the above and according to the method described in the Examples described below.

The agent for proliferating pancreatic β cells, containing the polynucleotide of the present invention, or a salt thereof, can be produced in the same manner as for the aforementioned medicament of the present invention, and can be safely administered to mammals.

<3> Use for Screening of a Prophylactic or Therapeutic Drug for Diabetes and the Like Since the polynucleotide of the present invention, or a salt thereof, has an activity to accelerate proliferation of pancreatic β cells, a substance that accelerates intracellular expression of the polynucleotide of the present invention also accelerates proliferation of pancreatic β cells, and is effective for the prophylaxis or treatment of diseases such as diabetes and the like. Therefore, the present invention provides a method for screening for a substance that proliferates pancreatic β cells, a prophylactic or therapeutic drug for diabetes (or a candidate substance thereof), which comprises comparing expression of the polynucleotide of the present invention in cells having an ability to express said polynucleotide in the presence or absence of a test substance.

The expression level of the polynucleotide of the present invention can be measured by detecting the polynucleotide of the present invention using a nucleic acid probe or nucleic acid primer that specifically detects the polynucleotide of the present invention (e.g., polynucleotide capable of hybridizing with the polynucleotide of the present invention under high stringent conditions (that is, nucleic acid containing a base sequence encoding the polynucleotide of the present invention or a part thereof, or a base sequence complementary to the base sequence encoding the polynucleotide of the present invention or a part thereof)).

Therefore, more specifically, the present invention provides a method for screening for a substance that proliferates pancreatic β cells or a prophylactic or therapeutic drug for diabetes (or a candidate substance thereof), comprising culturing cells having an ability to express the polynucleotide of the present invention in the presence or absence of a test substance, measuring and comparing the expression level of the polynucleotide of the present invention under both conditions by using a nucleic acid probe, nucleic acid primer or the like that specifically detects the polynucleotide of the present invention (hereinafter sometimes referred to as "the screening method of the present invention").

While the above-mentioned cells having an ability to express the polynucleotide of the present invention is not particularly limited as long as they are mammalian cells (e.g., human, mouse, rat, rabbit, sheep, swine, bovine, cat, dog, monkey) that endogenously express the polynucleotide of the present invention, for example, human pancreatic β cells are used. In addition, a tissue containing cells having an ability to express the polynucleotide of the present invention may also be used. Examples of the tissues include pancreatic islet containing pancreatic β cells, pancreas, lung, bladder, placenta, mammary gland, and colon. As the tissues, pancreatic islet containing pancreatic β cells, pancreas and the like are preferably used. When cells or tissues derived from a non-human animal are used, it may be isolated from the living organism and cultured, or a test substance may be administered to the living organism and the cells or tissues therein may be isolated after a certain time.

Examples of the test substances include protein, peptide, nonpeptidic compound, synthesis compound, fermentation product, cell extract, plant extract, animal tissue extract and the like. These substances may be novel or known. In addition, compound library produced using a combinatorial chemistry technique, random peptide library produced by solid phase synthesis or phage display, and the like are also preferable examples of the test substances.

For example, the expression level of the polynucleotide of the present invention level can be concretely measured as follows.

(i) A test substance is administered to a non-human mammal (e.g., mouse, rat, rabbit, sheep, swine, bovine, cat, dog, monkey, bird). At a certain time after administration, a biological sample containing cells that naturally express the polynucleotide of the present invention, such as islet, pancreas and the like, is recovered. The polynucleotide of the present invention which is expressed in the cells contained in the obtained biological sample can be quantified by, for example, preparing an RNA extract containing micro RNA from the cells by a conventional method, and subjecting the obtained RNA extract to RT-PCR, nucleic acid array, Northern blot analysis and the like.

(ii) Mammalian cells that express the polynucleotide of the present invention (e.g., pancreatic β cells) are cultivated in vitro according to a conventional method, during which a test substance is added to the medium. After culturing for a certain time, the expression level of the polynucleotide of the present invention, which is contained in the cells, can be quantified and analyzed using a method such as RT-PCR, nucleic acid array, Northern blot analysis and the like.

As a result of the measurement, changes in the expression level of the polynucleotide of the present invention, which is caused by the test substance, are correlated to an activity to proliferate pancreatic β cells, or an activity to prevent or treat diabetes. Thus, a substance that promoted expression of the polynucleotide of the present invention can be selected as a substance that proliferates pancreatic β cells or a prophylactic or therapeutic drug for diabetes (or a candidate substance thereof).

Optionally, whether the substance selected in the above-mentioned step has an activity to proliferate pancreatic β cells (including an activity to accelerate proliferation), or can prevent or treat diabetes may be confirmed.

The presence or absence of an activity to proliferate pancreatic β cells can be determined, for example, by culturing, in vitro, pancreatic β cells of a mammal in the presence or absence of a test substance and, at a certain time after the start of the culture, measuring the level of proliferation of pancreatic β cells under both conditions by a method known per se such as MTT assay and the like, and comparing them.

In addition, the presence or absence of an activity to prevent or treat diabetes can be determined by, for example, administering a test substance to a diabetes model non-human mammal and, at a certain time after administration, evaluating the symptoms of diabetes such as blood glucose in the non-human mammal, and comparing the symptoms with those without administration of the test substance.

Examples of the diabetes model non-human mammals include type 2 diabetes model mice such as KK mouse (e.g., KK/Ta mouse, KK/Snk mouse), KK-A$^y$ mouse (e.g., KK-A$^y$/Ta mouse), C57BL/KsJ db/db mouse, C57BL/6J db/db mouse, ob/ob mouse and high-fat diet-loaded mouse, and type 2 diabetes model rat such as GK rat, ZDF rat and high-fat diet-loaded rat. Examples of the diabetes model non-human mammals include type 1 diabetes animal models such as streptozotocin (STZ)-induced diabetes animal model and multiple low doses of STZ model.

Then, a test substance confirmed to have an activity to proliferate pancreatic β cells and/or an activity to prevent or treat diabetes can be selected as a substance that proliferates pancreatic β cells or a prophylactic or therapeutic drug for diabetes (or a candidate substance thereof).

A substance selected by the screening method of the present invention is useful as an agent for proliferating pancreatic β cells; an agent for the prophylaxis or treatment of diabetes (e.g., type 1 diabetes, type 2 diabetes, gestational diabetes, obese diabetes); an agent for the prophylaxis or treatment of impaired glucose tolerance (IGT); an agent for suppressing progression from impaired glucose tolerance to diabetes (or a candidate substance thereof).

In addition, a substance selected by the screening method of the present invention is also useful as an agent for the prophylaxis or treatment of diabetic complications [e.g., neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia hypacusis, hypacusis, cerebrovascular disorder, peripheral blood circulation disorder], diabetic cachexia, insulin resistance syndrome and the like (or a candidate substance thereof).

The substance selected by the screening method of the present invention can be formulated in the same manner as in the aforementioned medicament of the present invention. Since the thus-obtained preparation is safe and low toxic, it can be administered to, for example, mammals (e.g., human, rat, mouse, hamster, rabbit, sheep, goat, swine, bovine, horse, cat, dog, monkey, chimpanzee).

<4> Use for Evaluation of Susceptibility to Prophylactic or Therapeutic Drug for Diabetes etc.

Since the polynucleotide of the present invention, or a salt thereof, has an activity to accelerate proliferation of pancreatic β cells, susceptibility of a patient to a prophylactic or therapeutic drug for diabetes or a drug for proliferating pancreatic β cells can be determined by, in the decision of an administration design of a prophylactic or therapeutic drug for diabetes or a drug for proliferating pancreatic β cells and the like, contacting a prophylactic or therapeutic drug for diabetes or a drug for proliferating pancreatic β cells to be administered to a patient's cells, measuring the expression level of the polynucleotide of the present invention in the cells, and correlating the changes in the expression level and the susceptibility to the prophylactic or therapeutic drug for diabetes or the drug for proliferating pancreatic β cells. Therefore, the present invention provides a method for determining the susceptibility to a prophylactic or therapeutic drug for diabetes or a drug for proliferating pancreatic β cells, comprising comparing the expression of the polynucleotide of the present invention in cells having an ability to express the polynucleotide between the presence and the absence of a prophylactic or therapeutic drug for diabetes or a drug for proliferating pancreatic β cells (hereinafter sometimes to be referred to as "determination method of the present invention").

More specifically, the present invention provides a method for determining susceptibility to a prophylactic or therapeutic drug for diabetes or a drug for proliferating pancreatic β cells, comprising culturing cells having an ability to express the polynucleotide of the present invention in the presence or absence of a prophylactic or therapeutic drug for diabetes or a drug for proliferating pancreatic β cells, measuring the expression levels of the polynucleotide of the present invention under both conditions using a nucleic acid probe or nucleic acid primer that specifically detects the polynucleotide of the present invention, and comparing them.

In the determination method of the present invention, as cells having an ability to express the polynucleotide of the present invention, cells of a test subject (human or other mammal (e.g., mouse, rat, rabbit, sheep, swine, bovine, cat, dog, monkey)) scheduled for administration of a prophylactic or therapeutic drug for diabetes or a drug for proliferating pancreatic β cells. The cells are not particularly limited as long as it naturally expresses the polynucleotide of the present invention (e.g., pancreatic β cell) or a biological sample containing same (e.g., islet, pancreas, lung, bladder, placenta, mammary gland, colon), with preference given to pancreatic β cell. Cell, tissues and the like derived from a mammal may be isolated from the body and cultured, or a prophylactic or therapeutic drug for diabetes or a drug for proliferating pancreatic β cells may be administered to a living organism and, after a certain time, the cells or a biological sample containing same may be isolated.

Examples of the prophylactic or therapeutic drugs for diabetes include those exemplified as the prophylactic or therapeutic drug for diabetes mentioned above.

Examples of the pancreatic β cell proliferating drugs include those exemplified as the prophylactic or therapeutic drug for diabetes mentioned above.

In the determination method of the present invention, the expression level of the polynucleotide of the present invention can be measured specifically as follows.

(i) A prophylactic or therapeutic drug for diabetes or a drug for proliferating pancreatic β cells is administered to human or a non-human mammal (e.g., mouse, rat, rabbit, sheep, swine, bovine, cat, dog, monkey, bird). At a certain time after administration, a biological sample containing cells that endogenously express the polynucleotide of the present invention, such as islets, pancreas and the like, are recovered by biopsy and the like. The polynucleotide of the present invention that is expressed in the cells contained in the collected biological sample can be quantified by, for example, extracting RNA containing miRNA from the cells etc. by a conventional method, and using a method such as RT-PCR, nucleic acid array and the like, or can also be quantified by Northernblot analysis known per se.

(ii) Mammalian cells (e.g., pancreatic β cells) that express the polynucleotide of the present invention are cultivated in vitro according to a conventional method in a medium added with a prophylactic or therapeutic drug for diabetes or a drug for proliferating pancreatic β cell. After cultivating for a certain time, and the expression level of the polynucleotide of the present invention contained in the cells can be quantified and analyzed by a method such as RT-PCR, nucleic acid array, Northern blot analysis and the like.

By the above-mentioned analysis, changes in the expression level of the polynucleotide of the present invention caused by a prophylactic or therapeutic drug for diabetes or a drug for proliferating pancreatic β cells, and the susceptibility to said prophylactic or therapeutic drug for diabetes or drug for proliferating pancreatic β cells are correlated. Then, based on the positive correlation between the changes in the expression level of the polynucleotide of the present invention, and the susceptibility to said prophylactic or therapeutic drug for diabetes or drug for proliferating pancreatic β cells, the susceptibility to said prophylactic or therapeutic drug for diabetes or drug for proliferating pancreatic β cells is determined.

When a prophylactic or therapeutic drug for diabetes or a drug for proliferating pancreatic β cells promotes expression level of the polynucleotide of the present invention, it can be determined that the test subject highly possibly has susceptibility to said prophylactic or therapeutic drug for diabetes or drug for proliferating pancreatic β cells (that is, the possibility is high that said prophylactic or therapeutic drug for diabetes or drug for proliferating pancreatic β cells is effective for the test subject). On the other hand, when the expression level of the polynucleotide of the present invention is not promoted, it can be determined that the test subject may not have susceptibility to said prophylactic or therapeutic drug for diabetes or drug for proliferating pancreatic β cells (that is, the possibility exists that said prophylactic or therapeutic drug for diabetes or drug for proliferating pancreatic β cells is ineffective for the test subject).

When the degree of promotion of the expression level of the polynucleotide of the present invention is higher, the test subject can be determined to have a higher possibility of having the susceptibility to said prophylactic or therapeutic drug for diabetes or drug for proliferating pancreatic β cells.

Using the determination method of the present invention, a prophylactic or therapeutic drug for diabetes and a drug for proliferating pancreatic β cells, which are expected to be effective for patients, can be decided in the determination of the administration plan of a prophylactic or therapeutic drug for diabetes or a drug for proliferating pancreatic β cells, selection of drug and the like.

A polypeptide containing the following base sequence can also be used as a prophylactic or therapeutic drug for diabetes or a drug for proliferating pancreatic β cells, in the same manner as with the polynucleotide of the present invention, and can be further used for a method for screening for a prophylactic or therapeutic drug for diabetes and the like, and a method for determining the susceptibility to a prophylactic or therapeutic drug for diabetes and the like.

<A> a base sequence having a homology of not less than 70% with the base sequence shown by SEQ ID NO: 1, 2, 3 or 4;

<B> a continuous partial sequence having a length of not less than 5 nucleotides, which is contained in the base sequence shown by SEQ ID NO: 1, 2, 3 or 4;

<C> a base sequence complementary to the base sequence of the above-mentioned <A> or <B>.

The base sequence of the aforementioned <A> has a homology (i.e., identity) of not less than 70% and less than 90%, preferably not less than 75% and less than 90%, not less than 80% and less than 90%, not less than 85% and less than 90%, with the base sequence shown by SEQ ID NO: 1, 2, 3 or 4.

In addition, the base sequence of the aforementioned <A> encompasses the base sequence shown by SEQ ID NO: 1, 2, 3 or 4, except that 3, 4, 5 or 6 bases are deleted, substituted, added or inserted. Examples of the base sequences include (i) the base sequence shown by SEQ ID NO: 1, 2, 3 or 4, except that 3, 4, 5 or 6 bases are deleted, (ii) the base sequence shown by SEQ ID NO: 1, 2, 3 or 4, except that 3, 4, 5 or 6 bases are added, (iii) the base sequence shown by SEQ ID NO: 1, 2, 3 or 4, except that 3, 4, 5 or 6 bases are inserted, (iv) the base sequence shown by SEQ ID NO: 1, 2, 3 or 4, except that 3, 4, 5 or 6 bases are substituted by other bases, and (v) the base sequences containing those mutations in combination (total number of bases deleted, substituted, added or inserted is 3, 4, 5 or 6).

When the base sequence contains mutations (deletion, substitution, addition or insertion) as mentioned above, there is no restriction regarding the positions of the mutations.

The length of the partial sequence of the aforementioned <B> is at least 5 nucleotides, preferably, not less than 7 nucleotides, not less than 10 nucleotides, not less than 12 nucleotides, not less than 15 nucleotides or not less than 17 nucleotides.

The position of the partial sequence of the aforementioned <B> in the base sequence shown by SEQ ID NO: 1, 2, 3 or 4 is not limited as long as the polynucleotide has an activity to accelerate proliferation of pancreatic β cells of a mammal. As an example of the position of the partial sequence of the aforementioned <B> in the base sequence shown by SEQ ID NO: 1, 2, 3 or 4, the 3'-terminal and 5'-terminal of the base sequence shown by SEQ ID NO: 1, 2, 3 or 4 can be mentioned.

As a preferable embodiment of the polynucleotide of the present invention containing a partial sequence of the aforementioned <B>, a polynucleotide consisting of a continuous partial sequence having a nucleotide length of not less than 5, which is contained in the base sequence shown by SEQ ID NO: 1, 2, 3 or 4, can be mentioned.

The base sequence of the aforementioned <C> is completely complementary to the base sequences of the above-mentioned <A> or <B>.

All references cited herein, including patents and patent applications, are hereby incorporated in full by reference, to the extent that they have been disclosed herein.

The present invention is explained in more detail in the following by referring to Examples, which are not to be construed as limitative.

EXAMPLES

The abbreviations in the Examples follow those currently in general use in the art and means, for example, as follows.
RNA: ribonucleic acid
miRNA: micro RNA
RT-PCR: Reverse Transcription-Polymerase Chain Reaction
BrdU: 5-bromo-2'-deoxyuridine
SEQ ID NOs in the Sequence Listing in the present description show the following sequences.
(SEQ ID NO: 1) base sequence of mmu-miR-199b*
(SEQ ID NO: 2) base sequence of mmu-miR-199b
(SEQ ID NO: 3) base sequence of mmu-miR-199a-5p
(SEQ ID NO: 4) base sequence of hsa-miR-199b-5p
(SEQ ID NO: 5) base sequence of precursor mmu-miR-199b
(SEQ ID NO: 6) base sequence of precursor hsa-miR-199b
(SEQ ID NO: 7) base sequence of precursor mmu-miR-199a-1
(SEQ ID NO: 8) base sequence of precursor mmu-miR-199a-2
(SEQ ID NO: 9) base sequence of precursor hsa-miR-199a-1
(SEQ ID NO: 10) base sequence of precursor hsa-miR-199a-2
(SEQ ID NO: 11) base sequence of primary transcript of mouse miR-199b
(SEQ ID NO: 12) base sequence of primary transcript of human miR-199b
(SEQ ID NO: 13) base sequence of primary transcript of mouse miR-199a
(SEQ ID NO: 14) base sequence of primary transcript of mouse miR-199a
(SEQ ID NO: 15) base sequence of primary transcript of human miR-199a
(SEQ ID NO: 16) base sequence of primary transcript of human miR-199a
(SEQ ID NO: 17) base sequence of the probe used in Example 3
(SEQ ID NO: 18) base sequence of the forward primer used in Example 3
(SEQ ID NO: 19) base sequence of the reverse primer used in Example 3
(SEQ ID NO: 20) base sequence of the probe used in Example 3
(SEQ ID NO: 21) base sequence of the forward primer used in Example 3
(SEQ ID NO: 22) base sequence of the reverse primer used in Example 3
(SEQ ID NO: 23) base sequence of the probe used in Example 3
(SEQ ID NO: 24) base sequence of the forward primer used in Example 3
(SEQ ID NO: 25) base sequence of the reverse primer used in Example 3
(SEQ ID NO: 26) base sequence of rno-mir-146b
(SEQ ID NO: 27) base sequence of hsa-mir-375

Example 1

A 0.7 mg/ml collagenaseP solution (Roche Diagnostics, Cat.11914428) was injected into the pancreas of male Wistar rats (9- to 12-week-old) via the common bile duct, and the pancreas was removed. The removed spleen was left standing at 37° C. for 20 min, and the pancreas tissue was disrupted by pipetting and washed with HBSS (Invitrogen). An islet cell suspension was prepared by density gradient centrifugation using Ficoll PM400 (Amersham Biotech). Rat primary culture islet cells were obtained from the above-mentioned islet cell suspension by using an enzyme solution for dispersing nerve cells (Nerve-Cell Culture System). The rat primary culture islet cells were suspended in DMEM (Invitrogen) containing 11 mM glucose, 1% horse serum (Invitrogen), 25 mM HEPES (Dojindo), and P.S. (Invitrogen). The above-mentioned islet cells suspended in DMEM were seeded on a 96-well plate coated with Matrigel-basement membrane (Becton, Dickinson and Company) at $2.0 \times 10^4$ cells/100 μl/well. On day 2 after seeding, the cells were transfected with Pre-miR miRNA Precursor (final concentration 2.5-50 nM, purchased from ABI, ID: PM10526) which expresses mmu-miR-199b* or Pre-miR Neg control #1 (10 nM, purchased from ABI, ID: AM17110) using 0.2 μl/well DharmaFECT1 (Thermo Scientific) in the presence of BrdU (final concentration 10 μM) and, 24 hr from the transfection, the medium was changed to the above-mentioned DMEM added with 10 μM BrdU. The IDs and the base sequences of the mature miRNAs of the Pre-miR miRNA Precursors used in Example 1 and the below-mentioned Example 2 are shown in Table 1. The expression level of the mmu-miR-199b* mRNA after the aforementioned transfection was analyzed as follows. That is, 2 days after the transfection, cDNA was prepared according to the attached protocol of TaqMan MicroRNA Cells-to-Ct™kit (Ambion) from the islet cells after transfection, and applied to quantitative RT-PCR method (ABI prism 7900 Sequence Detection System, ABI) using TaqMan miRNA assays (ABI). The ID of the aforementioned TaqMan miRNA assay (ABI) is shown in Table 1.

TABLE 1

| mature miRNA name | accession # | base sequence of mature miRNA | Pre-miR ID | TaqMan ID |
|---|---|---|---|---|
| Pre-miR Neg control #1 | | | AM17110 | |
| mmu-miR-199b* | MIMAT0000672 | CCCAGUGUUUAGACUACCUGUUC (SEQ ID NO: 1) | PM10526 | 001131 |
| hsa-miR-199a-3p | MIMAT0000232 | ACAGUAGUCUGCACAUUGGUUA (SEQ ID NO: 2) | PM11779 | 002304 |
| hsa-miR-199a-5p | MIMAT0000231 | CCCAGUGUUCAGACUACCUGUUC (SEQ ID NO: 3) | PM10893 | 000498 |
| hsa-miR-199b-5p | MIMAT0000263 | CCCAGUGUUUAGACUAUCUGUUC (SEQ ID NO: 4) | PM10553 | 000500 |

As shown in FIG. 1, the expression level of mmu-miR-199b* increased remarkably in a manner dependent on the concentration of introduced Pre-miR miRNA Precursor that expresses mmu-miR-199b*.

Example 2

The rat primary culture islet cells prepared in the same manner as in Example 1 were transfected with final concentration 2.5-50 nM of Pre-miR miRNA Precursor that expresses mmu-miR-199b* (purchased from ABI, ID: PM10526), Pre-miR miRNA Precursor that expresses hsa-miR-199a-3p (purchased from ABI, ID: PM11779), Pre-miR miRNA Precursor that expresses hsa-miR-199a-5p (purchased from ABI, ID: PM10893) or Pre-miR miRNA Precursor that expresses hsa-miR-199b-5p (purchased from ABI, ID: PM10553), or 10 nM Pre-miR Neg control #1 (purchased from ABI, ID: AM17110), and the activity to accelerate proliferation of pancreatic β cells was evaluated on day 5 from the transfection. The activity to accelerate proliferation of pancreatic β cells was specifically evaluated as follows. That is, 5 days from the aforementioned transfection, the rat primary culture islet cells were immersed in 4% para-formaldehyde (Wako Pure Chemical Industries, Ltd.) at room temperature for 30 min, and immersed in 1.5N HCl solution for 1 hr. Then, the cells were immersed in PBS (Invitrogen) containing 10% normal goat serum (GIBCO, hereinafter to be referred to as NGS.) and 0.2% Triton X-100 (Sigma) at room temperature for 20 min. Furthermore, a solution of guinea pig polyclonal anti-insulin antibody (ABCAM) and mouse monoclonal anti-BrdU antibody (Dako) diluted 200-fold with 1% NGS containing PBS was reacted at 4° C. overnight, and the cells were washed three times with PBS (200 μl/well). 200-fold diluted goat anti-guinea pig Alexa fluor 568 (Invitrogen) and goat anti-mouse Alexa fluor 488 (Invitrogen), and 5 μM Hoechst33342 (Invitrogen) in 1% NGS-containing PBS were reacted at room temperature for 1 hr. The cells were washed three times with PBS (200 μl/well), and subjected to analysis by IN Cell Analyzer 1000 (GE Healthcare), and 20 fields of images per 1 well were obtained using ×10 objective lens. Using Developer soft ware, about 3000-4000 cells of the insulin positive cells and about 500 cells of the insulin positive and BrdU positive cells were analyzed per each well.

Figure 2:
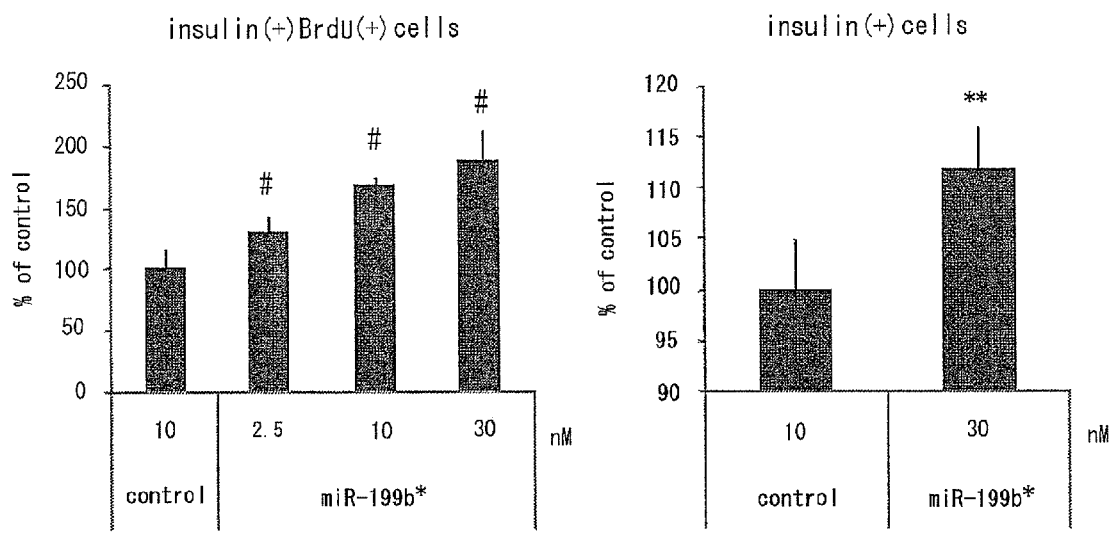
FIG. 2 shows increase of insulin positive and BrdU positive cell number, and insulin positive cell number in rat primary culture islet cells transfected with Pre-miR miRNA Precursor that expresses mmu-miR-199b*. For statistical processing relating to concentration dependency, parametric Williams test was used (# means significant), and for statistical processing of other items, t-test was used (* shows $0.01<P<0.05$, ** shows $P<0.01$).
Figure 3:
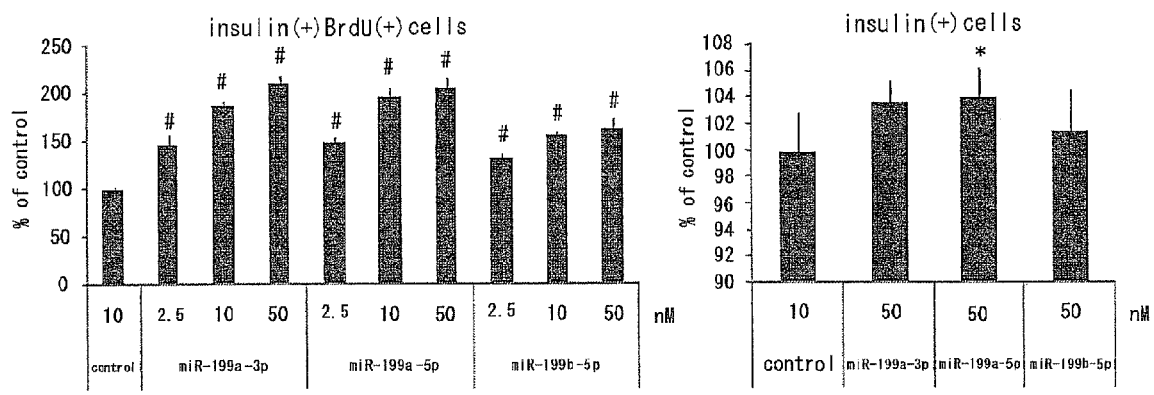
FIG. 3 shows increase of insulin positive and BrdU positive cell number in rat primary culture islet cells transfected with Pre-miR miRNA Precursor that expresses hsa-miR-199a-3p, Pre-miR miRNA Precursor that expresses hsa-miR-199a-5p or Pre-miR miRNA Precursor that expresses hsa-miR-199b-5p. For statistical processing relating to concentration dependency, parametric Williams test was used (# means significant), and for statistical processing of other items, t-test was used (* shows $0.01<P<0.05$, ** shows $P<0.01$).

The results obtained by the above-mentioned analysis are shown in FIG. 2. As shown in FIG. 2, due to the expression of mmu-miR-199b*, the number of the insulin positive and BrdU positive cells significantly increased in a concentration-dependent manner, and the number of the insulin positive cells significantly increased by the 50 nM treatment. Therefore, it was shown that pancreatic β cells proliferate as the gene expression of mmu-miR-199b* increases. Furthermore, as shown in FIG. 3, it was found that forced expression of hsa-miR-199a-3p, hsa-miR-199a-5p or hsa-miR-199b-5p significantly increased the number of the insulin positive and BrdU positive cells in a manner dependent on the concentration of each Pre-miR miRNA Precursor subjected to the transfection, and proliferated the pancreatic β cells in the same manner as with mmu-miR-199b*.

Example 3

In the same manner as in Example 1, the rat primary culture islet cells were transfected with Pre-miR miRNA Precursor that expresses mmu-miR-199b* (final concentration 2.5-50 nM, purchased from ABI, ID: PM10526) or 10 nM Pre-miR Neg control #1 (purchased from ABI, ID: AM17110). On day 2 from the transfection, total RNA was extracted using RNeasy96 (Qiagen) from the islet cells after said transfection. cDNA was synthesized from the total RNA using a PrimeScript RT reagent kit (Takara). Using the cDNA, a quantitative RT-PCR method (ABI prism 7900 Sequence Detection System, ABI) was performed, and the mRNA expression level of cyclin D1 and cyclin E2 genes per TATA binding protein (TBP) genes was calculated. The sequences of probes and primers used for the present analysis are shown in Table 2.

TABLE 2

| gene | probe | forward | reverse |
|------|-------|---------|---------|
| rTBP | 5'-Fam-CCACAGGGTGCCATGACTC (SEQ ID NO: 17) | 5'-CTTCCACCTTATGCTCAG (SEQ ID NO: 18) | 5'-GACTGAAGATGGGAATTC (SEQ ID NO: 19) |
| rCyclin D1 | 5'-Fam-AGAACAAGCAGATCATCCGCAA (SEQ ID NO: 20) | 5'-CACTTCCTCTCCAAAATG (SEQ ID NO: 21) | 5'-GGGTTGGAAATGAACTTC (SEQ ID NO: 22) |
| rCyclin E2 | 5'-Fam-CAGAGGAGATCACCAAGAAGCATC (SEQ ID NO: 23) | 5'-CCAAGAAGAGAAAAACAGC (SEQ ID NO: 24) | 5'-GCCAACAATTCCTAATCTC (SEQ ID NO: 25) |

Figure 4:
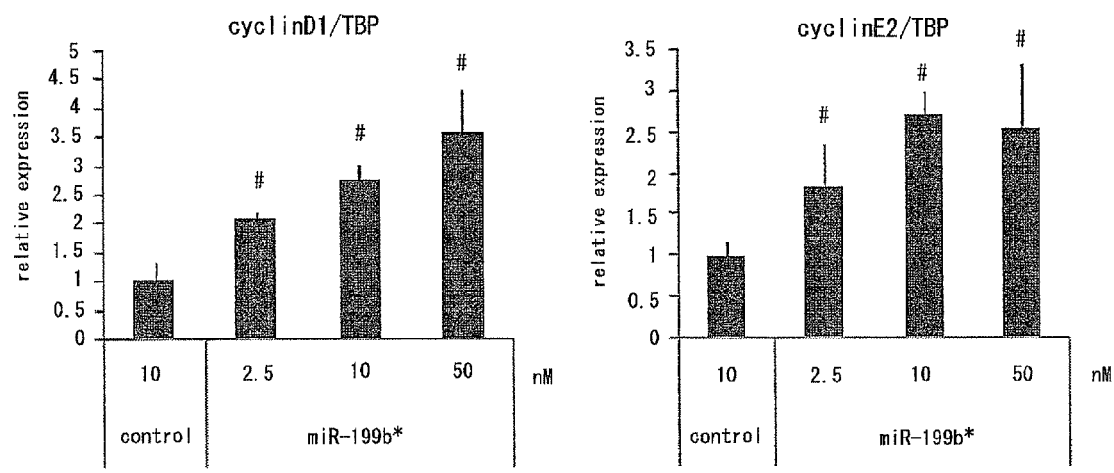
FIG. 4 shows increase of expression of cyclin D1 and cyclin E2 genes in rat primary culture islet cells transfected with Pre-miR miRNA Precursor that expresses mmu-miR-199b*. For statistical processing, parametric Williams test was used (# means significant).

The results of the above-mentioned calculation are shown in FIG. 4. As shown in FIG. 4, it was found that mmu-miR-199b* promoted expression of cyclin D1 and cyclin E2 genes in a manner dependent on the concentration of the introduced precursor miRNA, and proliferated pancreatic β cells.

Reference Example

Using a method equivalent to that in the above-mentioned Examples 1 to 3, it was shown that rno-mir-146b and hsa-mir-375, for which IDs and base sequences are shown in the following Table 3, also have an activity to accelerate proliferation of pancreatic β cells.

TABLE 3

| miRNA name | accession # | mature sequence |
|------------|-------------|-----------------|
| Pre-miR Neg control #1 | | |
| rno-mir-146b | MIMAT0005595 | UGAGAACUGAAUUCCAUAGGCUGU (SEQ ID NO: 26) |
| hsa-mir-375 | MIMAT0000728 | UUUGUUCGUUCGGCUCGCGUGA (SEQ ID NO: 27) |

From these results, it was suggested that mature miR-146b, mature miR-375 and precursors thereof can also be used as a prophylactic or therapeutic drug for diabetes or an agent for proliferating pancreatic β cells, like the polynucleotide of the present invention. In addition, it was also suggested that mature miR-146b, mature miR-375 and precursors thereof can be used for screening for a prophylactic or therapeutic drug for diabetes and the like, and determination of the susceptibility to a prophylactic or therapeutic drug for diabetes and the like.

INDUSTRIAL APPLICABILITY

According to the present invention, a new prophylaxis or therapeutic drug for diseases such as diabetes and the like is provided. In addition, a method for screening for a prophylaxis or therapeutic drug for diabetes and the like, and a method for determining the susceptibility to a prophylactic or therapeutic drug for diabetes and the like, which are based on a new scientific theory, are provided.

This application is based on patent application No. 2010-156261 (filing date: Jul. 8, 2010) filed in Japan, the contents of which are encompassed in full herein.

The invention claimed is:

1. A method for the treatment of diabetes in a mammal having diabetes, comprising administering an effective amount of a polynucleotide comprising a base sequence the same as or having a homology of not less than 90% to the base sequence shown by SEQ ID NO: 1, 2, 3 or 4, or a salt thereof, to said mammal.

2. A method for proliferating pancreatic β cells in a mammal having diabetes, comprising administering an effective amount of a polynucleotide comprising a base sequence the same as or having a homology of not less than 90% to the base sequence shown by SEQ ID NO: 1, 2, 3 or 4, or a salt thereof, to said mammal.

3. The method according to claim 1, wherein the diabetes is type 1 diabetes.

4. The method according to claim 1, wherein the polynucleotide comprises a base sequence shown by SEQ ID NO: 1, 2, 3 or 4.

5. The method according to claim 2, wherein the polynucleotide comprises a base sequence shown by SEQ ID NO: 1, 2, 3 or 4.

* * * * *

SEQUENCE LISTING

```
<160> NUMBER OF SEQ ID NOS: 27

<210> SEQ ID NO 1
<211> LENGTH: 23
<212> TYPE: RNA
<213> ORGANISM: Mus musculus

<400> SEQUENCE: 1
cccaguguuu agacuaccug uuc                                              23

<210> SEQ ID NO 2
<211> LENGTH: 22
<212> TYPE: RNA
<213> ORGANISM: Mus musculus

<400> SEQUENCE: 2
acaguagucu gcacauuggu ua                                               22

<210> SEQ ID NO 3
<211> LENGTH: 23
<212> TYPE: RNA
<213> ORGANISM: Mus musculus

<400> SEQUENCE: 3
cccaguguuc agacuaccug uuc                                              23

<210> SEQ ID NO 4
<211> LENGTH: 23
<212> TYPE: RNA
<213> ORGANISM: Homo sapiens

<400> SEQUENCE: 4
cccaguguuu agacuaucug uuc                                              23

<210> SEQ ID NO 5
<211> LENGTH: 110
<212> TYPE: RNA
<213> ORGANISM: Mus musculus

<400> SEQUENCE: 5
ccagaggaua ccuccacucc gucuacccag uguuuagacu accguucag gacucccaaa       60 uuguacagua gucugcacau ugguuaggcu gggcuggguu agacccucgg               110

<210> SEQ ID NO 6
<211> LENGTH: 110
<212> TYPE: RNA
<213> ORGANISM: Homo sapiens

<400> SEQUENCE: 6
ccagaggaca ccuccacucc gucuacccag uguuuagacu aucguucag gacucccaaa       60 uuguacagua gucugcacau ugguuaggcu gggcuggguu agacccucgg               110

<210> SEQ ID NO 7
```

```
<211> LENGTH: 70
<212> TYPE: RNA
<213> ORGANISM: Mus musculus

<400> SEQUENCE: 7
gccaucccag uguucagacu accuguucag gaggcuggga cauguacagu agucugcaca      60
uugguuaggc                                                             70

<210> SEQ ID NO 8
<211> LENGTH: 110
<212> TYPE: RNA
<213> ORGANISM: Mus musculus

<400> SEQUENCE: 8
uggaagcuuc aggagauccu gcuccgucgc cccaguguuc agacuaccug uucaggacaa      60
ugccguugua caguagucug cacauugguu agacugggca agggccagca                 110

<210> SEQ ID NO 9
<211> LENGTH: 71
<212> TYPE: RNA
<213> ORGANISM: Homo sapiens

<400> SEQUENCE: 9
gccaacccag uguucagacu accuguucag gaggcucuca auguguacag uagucugcac      60
auugguuagg c                                                           71

<210> SEQ ID NO 10
<211> LENGTH: 110
<212> TYPE: RNA
<213> ORGANISM: Homo sapiens

<400> SEQUENCE: 10
aggaagcuuc uggagauccu gcuccgucgc cccaguguuc agacuaccug uucaggacaa      60
ugccguugua caguagucug cacauugguu agacugggca agggagagca                 110

<210> SEQ ID NO 11
<211> LENGTH: 137
<212> TYPE: DNA
<213> ORGANISM: Mus musculus

<400> SEQUENCE: 11
tgctgcctgg atggaccaga ggatacctcc actccgtcta cccagtgttt agactacctg      60
ttcaggactc ccaaattgta cagtagtctg cacattggtt aggctgggct gggttagacc      120
ctcggcaccg tcgctgg                                                     137

<210> SEQ ID NO 12
<211> LENGTH: 137
<212> TYPE: DNA
<213> ORGANISM: Homo sapiens

<400> SEQUENCE: 12
cagtggcggc ggtgccgagg gtctaaccca gcccagccta accaatgtgc agactactgt      60
acaatttggg agtcctgaac agatagtcta aacactgggt agacggagtg gaggtgtcct     120
ctggtccatc caggcag                                                     137

<210> SEQ ID NO 13
<211> LENGTH: 87
<212> TYPE: DNA
<213> ORGANISM: Mus musculus
```

```
<400> SEQUENCE: 13
cccaagccca gcctaaccaa tgtgcagact actgtacatg tcccagcctc ctgaacaggt      60
agtctgaaca ctgggatggc ggggatg                                          87

<210> SEQ ID NO 14
<211> LENGTH: 137
<212> TYPE: DNA
<213> ORGANISM: Mus musculus

<400> SEQUENCE: 14
ttttccacac accgatggaa gcttcaggag atcctgctcc gtcgcccag tgttcagact       60 acctgttcag gacaatgccg ttgtacagta gtctgcacat tggttagact gggcaagggc    120
cagcaacgcc atggacg                                                    137

<210> SEQ ID NO 15
<211> LENGTH: 88
<212> TYPE: DNA
<213> ORGANISM: Homo sapiens

<400> SEQUENCE: 15
ccaagcccag cctaaccaat gtgcagacta ctgtacacat tgagagcctc ctgaacaggt      60
agtctgaaca ctgggttggc ggggccgg                                         88

<210> SEQ ID NO 16
<211> LENGTH: 137
<212> TYPE: DNA
<213> ORGANISM: Homo sapiens

<400> SEQUENCE: 16
gcggtccatg gcgttgctct cccttgccca gtctaaccaa tgtgcagact actgtacaac      60
ggcattgtcc tgaacaggta gtctgaacac tggggcgacg gagcaggatc tccagaagct    120
tccttctatg tacttaa                                                    137

<210> SEQ ID NO 17
<211> LENGTH: 19
<212> TYPE: DNA
<213> ORGANISM: Artificial
<220> FEATURE:
<223> OTHER INFORMATION: rTBP Taqman probe

<400> SEQUENCE: 17
ccacagggtg ccatgactc                                                   19

<210> SEQ ID NO 18
<211> LENGTH: 18
<212> TYPE: DNA
<213> ORGANISM: Artificial
<220> FEATURE:
<223> OTHER INFORMATION: rTBP Taqman forward primer

<400> SEQUENCE: 18
cttccaccct tatgctcag                                                   18

<210> SEQ ID NO 19
<211> LENGTH: 18
<212> TYPE: DNA
<213> ORGANISM: Artificial
<220> FEATURE:
<223> OTHER INFORMATION: rTBP Taqman reverse primer
```

```
<400> SEQUENCE: 19
gactgaagat gggaattc                                                    18

<210> SEQ ID NO 20
<211> LENGTH: 22
<212> TYPE: DNA
<213> ORGANISM: Artificial
<220> FEATURE:
<223> OTHER INFORMATION: rCyclinD1 Taqman probe

<400> SEQUENCE: 20
agaacaagca gatcatccgc aa                                               22

<210> SEQ ID NO 21
<211> LENGTH: 18
<212> TYPE: DNA
<213> ORGANISM: Artificial
<220> FEATURE:
<223> OTHER INFORMATION: rCyclinD1 Taqman forward primer

<400> SEQUENCE: 21
cacttcctct ccaaaatg                                                    18

<210> SEQ ID NO 22
<211> LENGTH: 18
<212> TYPE: DNA
<213> ORGANISM: Artificial
<220> FEATURE:
<223> OTHER INFORMATION: rCyclinD1 Taqman reverse primer

<400> SEQUENCE: 22
gggttggaaa tgaacttc                                                    18

<210> SEQ ID NO 23
<211> LENGTH: 24
<212> TYPE: DNA
<213> ORGANISM: Artificial
<220> FEATURE:
<223> OTHER INFORMATION: rCyclinE2 Taqman probe

<400> SEQUENCE: 23
cagaggagat caccaagaag catc                                             24

<210> SEQ ID NO 24
<211> LENGTH: 19
<212> TYPE: DNA
<213> ORGANISM: Artificial
<220> FEATURE:
<223> OTHER INFORMATION: rCyclinE2 Taqman forward primer

<400> SEQUENCE: 24
ccaagaagag aaaaacagc                                                   19

<210> SEQ ID NO 25
<211> LENGTH: 19
<212> TYPE: DNA
<213> ORGANISM: Artificial
<220> FEATURE:
<223> OTHER INFORMATION: rCyclinE2 Taqman reverse primer

<400> SEQUENCE: 25
gccaacaatt cctaatctc                                                   19

<210> SEQ ID NO 26
<211> LENGTH: 24
```

```
<212> TYPE: RNA
<213> ORGANISM: Rattus norvegicus

<400> SEQUENCE: 26
ugagaacuga auuccauagg cugu                                          24

<210> SEQ ID NO 27
<211> LENGTH: 22
<212> TYPE: RNA
<213> ORGANISM: Homo sapiens

<400> SEQUENCE: 27
uuuguucguu cggcucgcgu ga                                            22
```